(12) United States Patent
Tuksar et al.

(10) Patent No.: US 8,802,854 B2
(45) Date of Patent: Aug. 12, 2014

(54) CRYSTALLINE FORMS OF PRASUGREL SALTS

(75) Inventors: Mihaela Tuksar, Cakovec (HR); Tomislav Biljan, Krizevci (HR); Miroslav Zegarac, Zagreb (HR)

(73) Assignee: Teva Pharmaceutical Industries Ltd., North Wales, PA (US)

( * ) Notice: Subject to any disclaimer, the term of this patent is extended or adjusted under 35 U.S.C. 154(b) by 0 days.

(21) Appl. No.: 13/639,453

(22) PCT Filed: Apr. 7, 2011

(86) PCT No.: PCT/US2011/031602
§ 371 (c)(1),
(2), (4) Date: Dec. 17, 2012

(87) PCT Pub. No.: WO2011/127300
PCT Pub. Date: Oct. 13, 2011

(65) Prior Publication Data
US 2013/0085154 A1    Apr. 4, 2013

Related U.S. Application Data

(60) Provisional application No. 61/322,165, filed on Apr. 8, 2010, provisional application No. 61/326,882, filed on Apr. 22, 2010, provisional application No. 61/348,914, filed on May 27, 2010, provisional application No. 61/355,304, filed on Jun. 16, 2010.

(51) Int. Cl.
*A61K 31/44*    (2006.01)
*C07D 471/02*    (2006.01)
*C07D 495/04*    (2006.01)

(52) U.S. Cl.
CPC ................... *C07D 495/04* (2013.01)
USPC .......................... 546/113; 514/301

(58) Field of Classification Search
CPC ................................................... C07D 495/04
See application file for complete search history.

(56) References Cited

U.S. PATENT DOCUMENTS

| 5,288,726 A | 2/1994 | Koike |
| 6,693,115 B2 | 2/2004 | Asai |
| 2012/0095035 A1 * | 4/2012 | Yuan et al. ..................... 514/301 |

FOREIGN PATENT DOCUMENTS

| CN | 101255169 A | 9/2008 |
| CN | 101899056 A | 12/2010 |
| GB | 2469883 A | 11/2010 |
| WO | WO 2007/114526 A1 | 10/2007 |
| WO | WO 2008/000418 A2 | 1/2008 |
| WO | WO 2009/062044 A2 | 5/2009 |
| WO | WO 2009/066326 A2 | 5/2009 |
| WO | WO 2009/098142 A1 | 8/2009 |
| WO | WO 2009/129983 A1 | 10/2009 |
| WO | WO 2009/130289 A1 | 10/2009 |
| WO | WO 2010/015144 A1 | 2/2010 |
| WO | WO 2010/070677 A2 | 6/2010 |
| WO | WO 2010/094471 A1 | 8/2010 |
| WO | WO 2010/111951 A1 | 10/2010 |
| WO | WO 2011/004392 A1 | 1/2011 |
| WO | WO 2011/057592 A1 | 5/2011 |
| WO | WO 2011/057593 A2 | 5/2011 |
| WO | WO 2011/127300 A1 | 10/2011 |

OTHER PUBLICATIONS

Zhaopeng Liu et al, "Method for Preparing Salts of Prasugrel", Chemical Abstracts Service, Columbus, Ohio, US.
Brittain, H.G., "Polymorphism in Pharmaceutical Solids", 1999, New York, Marcel Dekker, Inc. , 236.

* cited by examiner

*Primary Examiner* — Heidi Reese
(74) *Attorney, Agent, or Firm* — Baker & Hostetler

(57) ABSTRACT

Salts of prasugrel were prepared including, for example, crystalline forms of prasugrel hydrobromide. These salts are useful, for example, in medicaments that inhibit the aggregation of platelets.

10 Claims, 25 Drawing Sheets

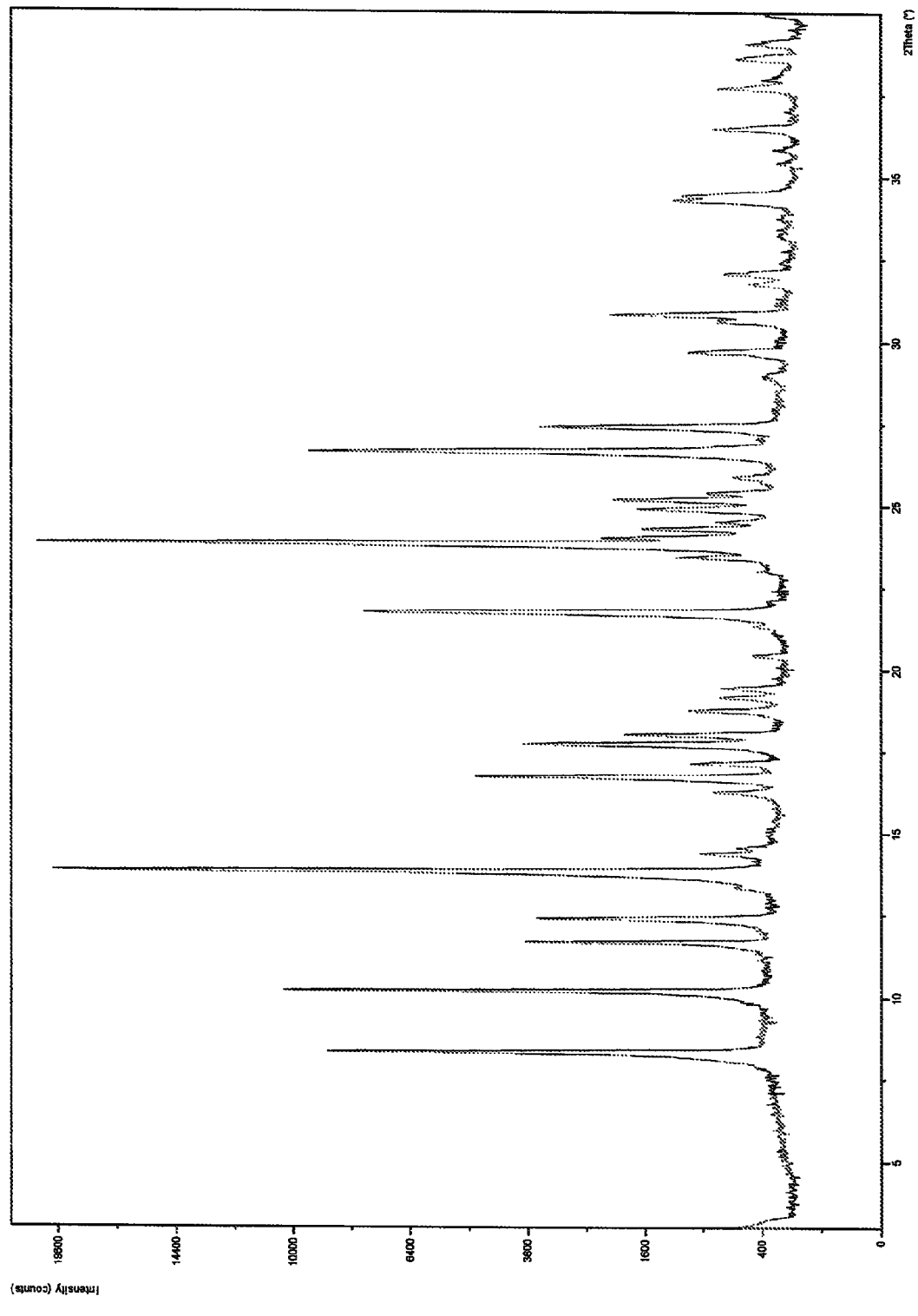
Figure 1: X-ray powder diffraction pattern of crystalline Prasugrel hydrochloride nitromethane solvate

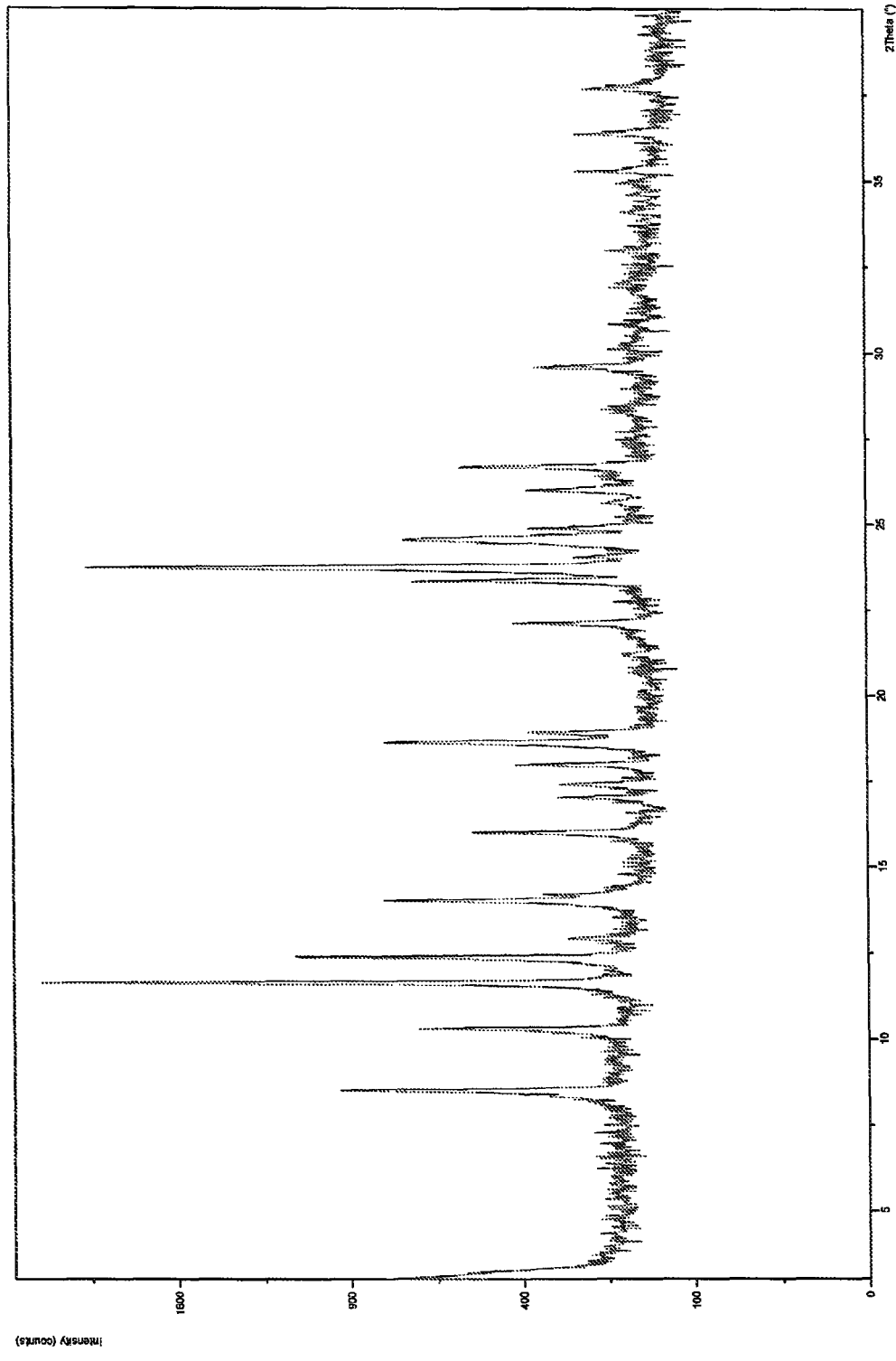
Figure 2: X-ray powder diffraction pattern of crystalline Form F of Prasugrel hydrochloride

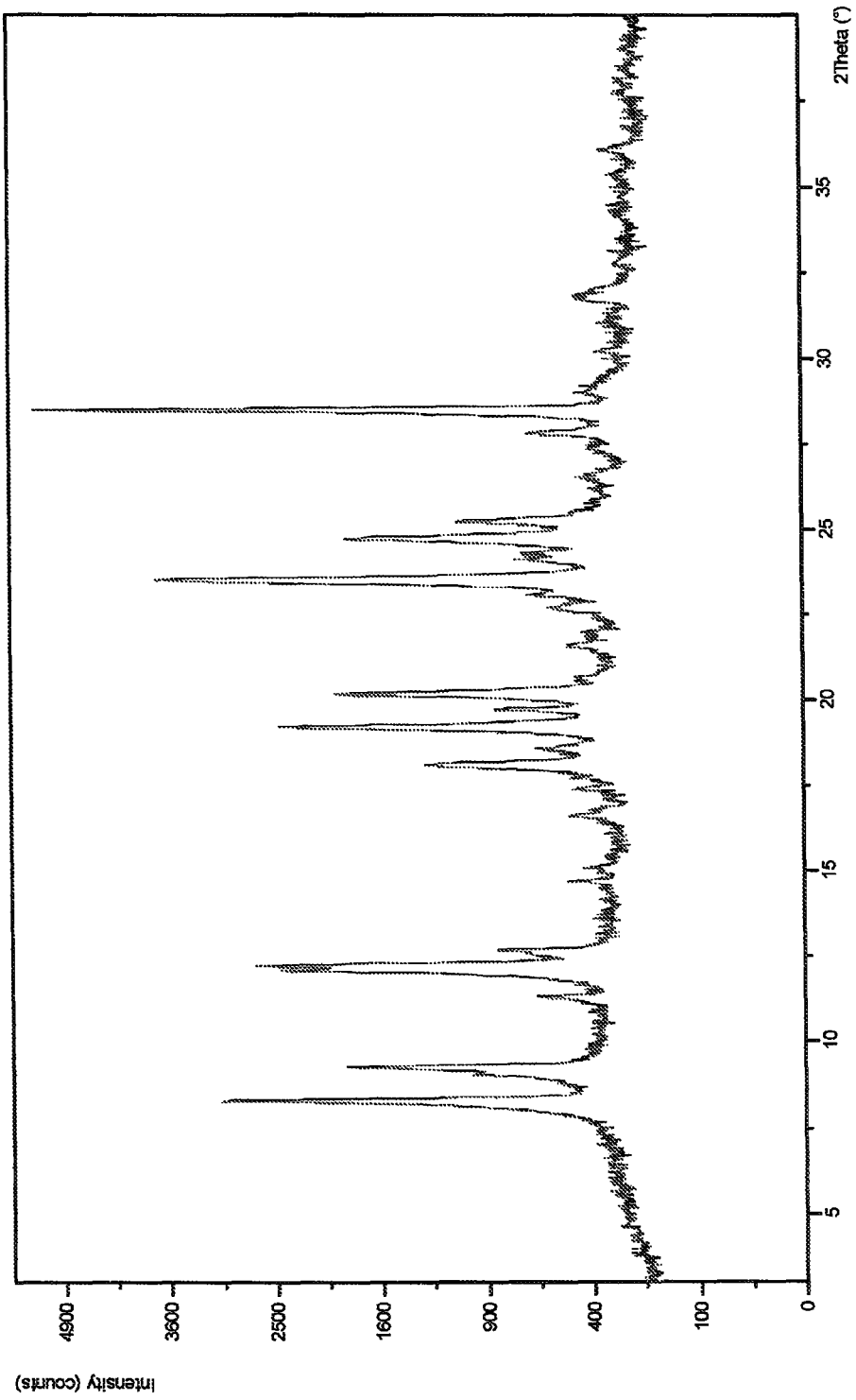
Figure 3: X-ray powder diffraction pattern for crystalline Prasugrel nitrate.
* The peak at 28.46 degrees 2-theta corresponds to the silica powder used as an internal standard.

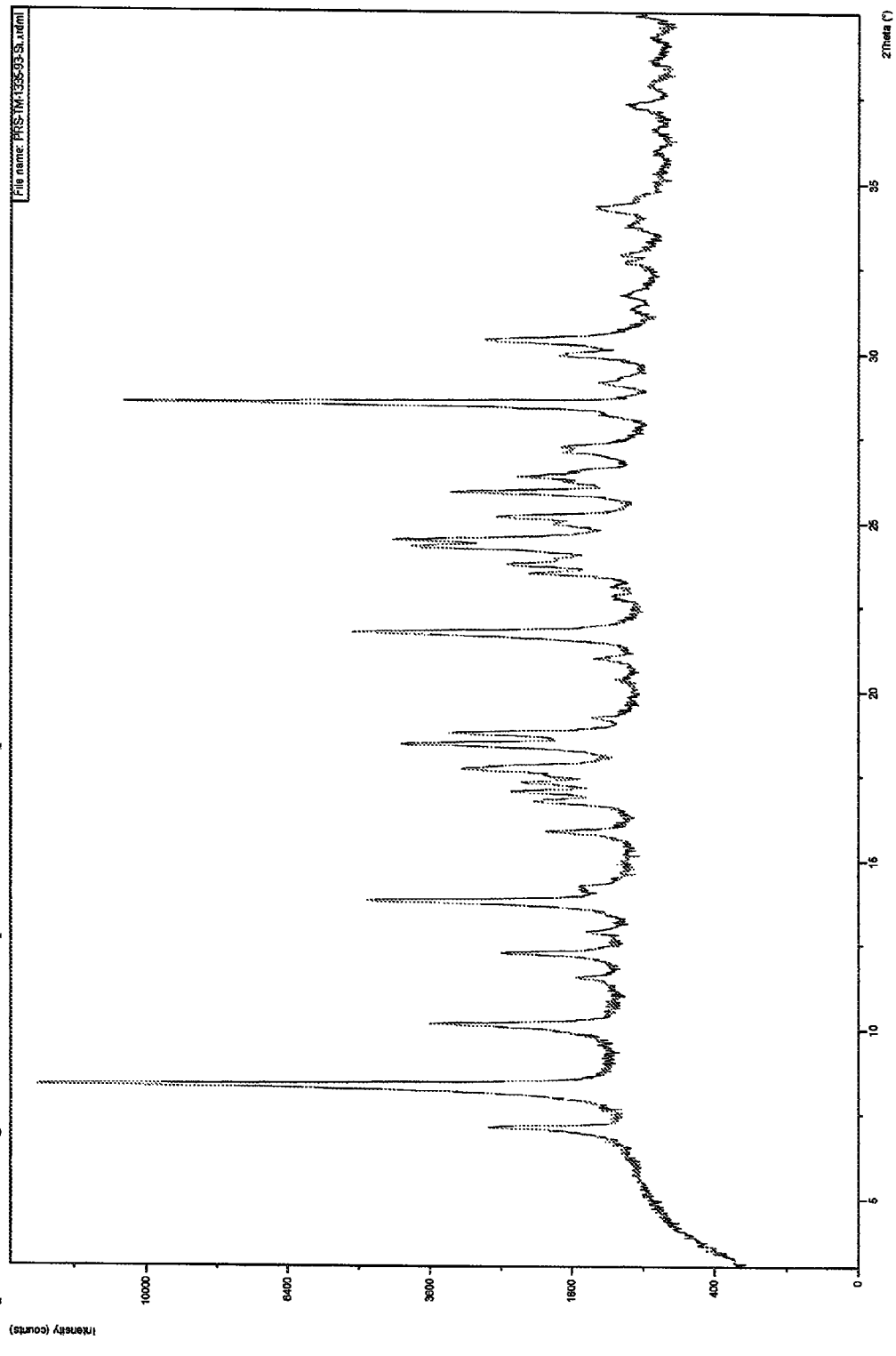
Figure 4: X-ray powder diffraction pattern of Form II of Prasugrel hydrobromide.
* The peak at 28.47 degrees 2-theta corresponds to the silica powder used as an internal standard.

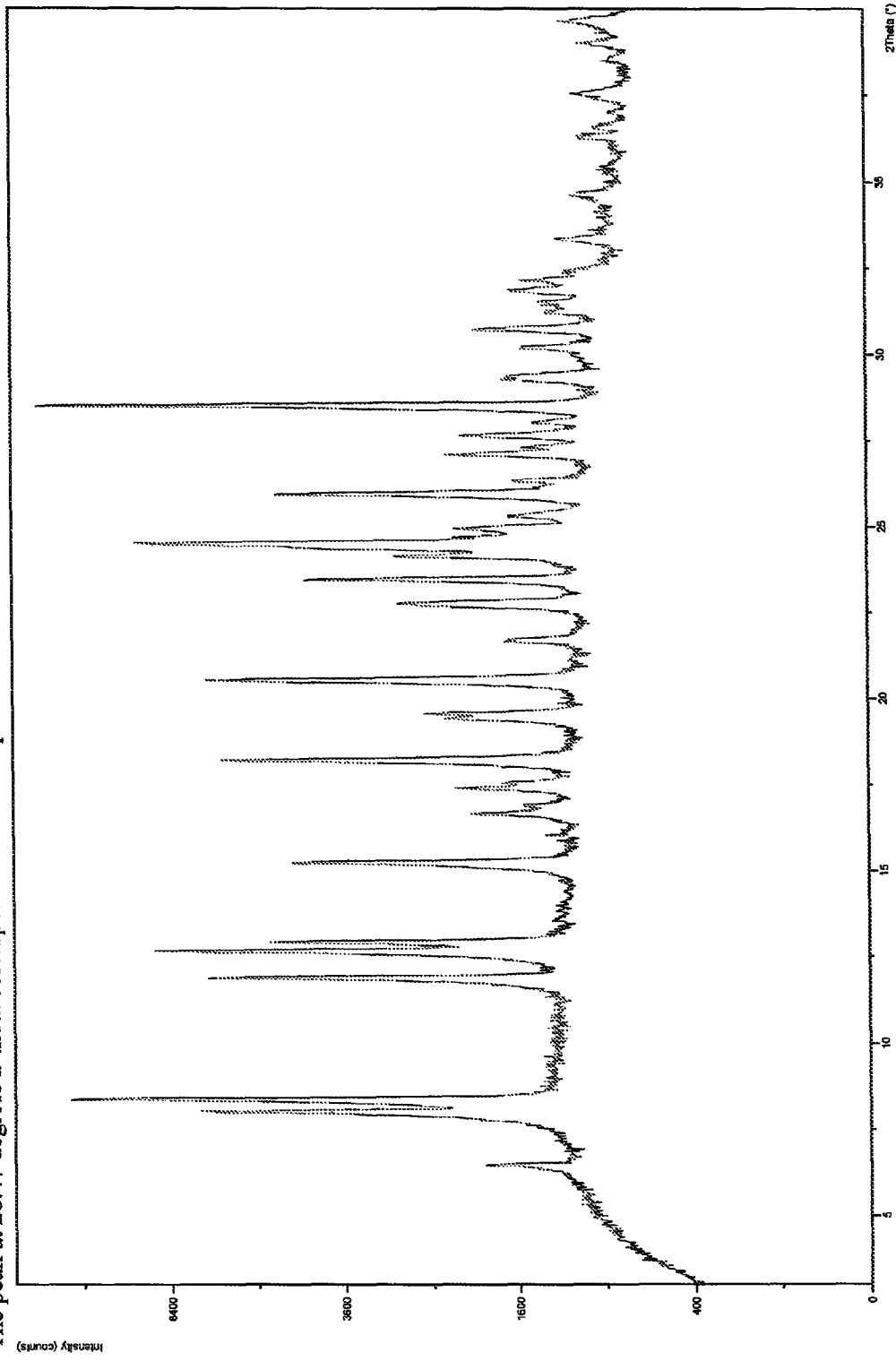
Figure 5: X-ray powder diffraction pattern of form III of Prasugrel hydrobromide
* The peak at 28.47 degrees 2-theta corresponds to the silica powder used as an internal standard.

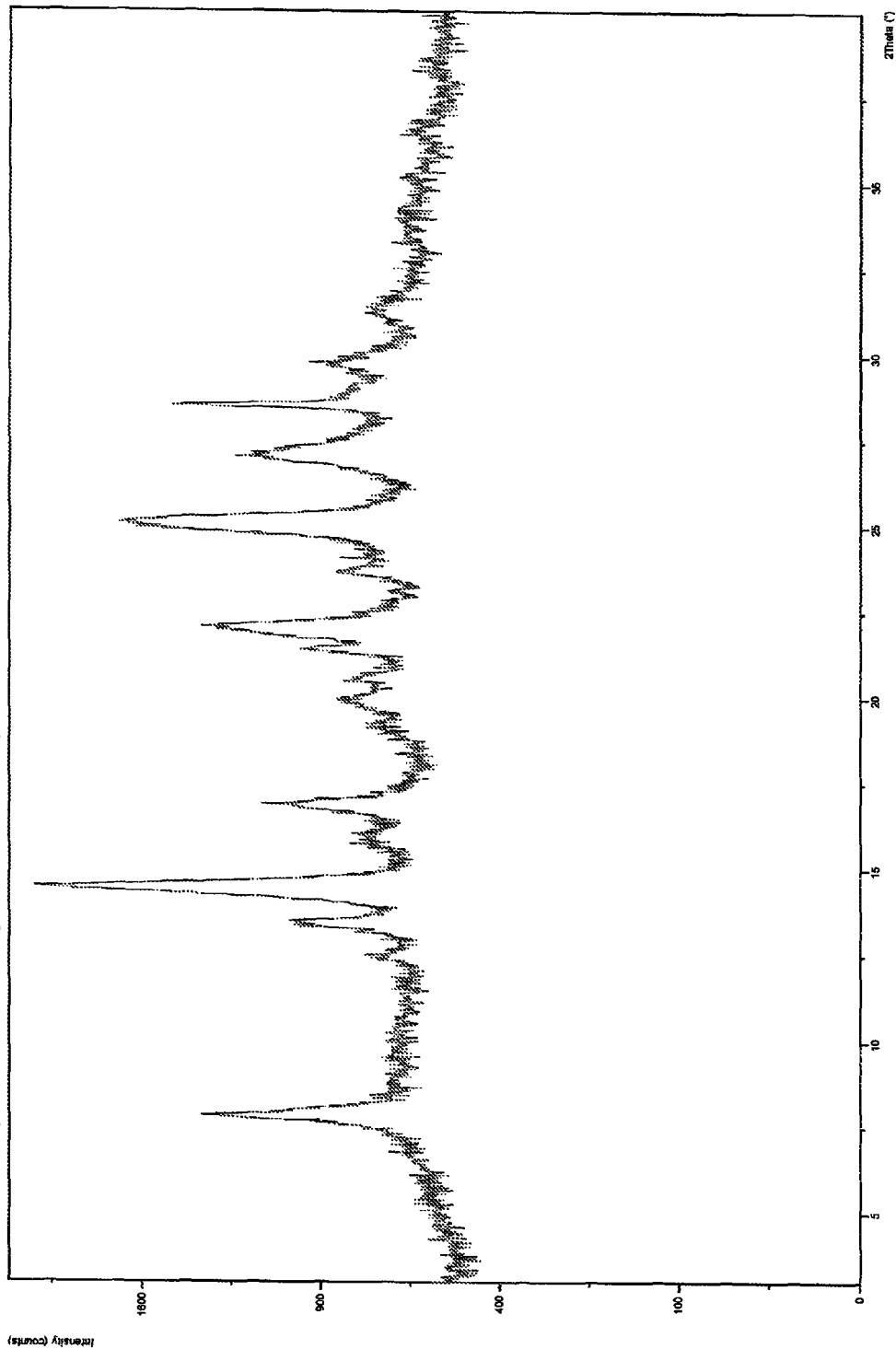
Figure 6: X-ray powder diffraction pattern of form I of Prasugrel hydrobromide.
* The peak at 28.50 degrees 2-theta corresponds to the silica powder used as an internal standard.

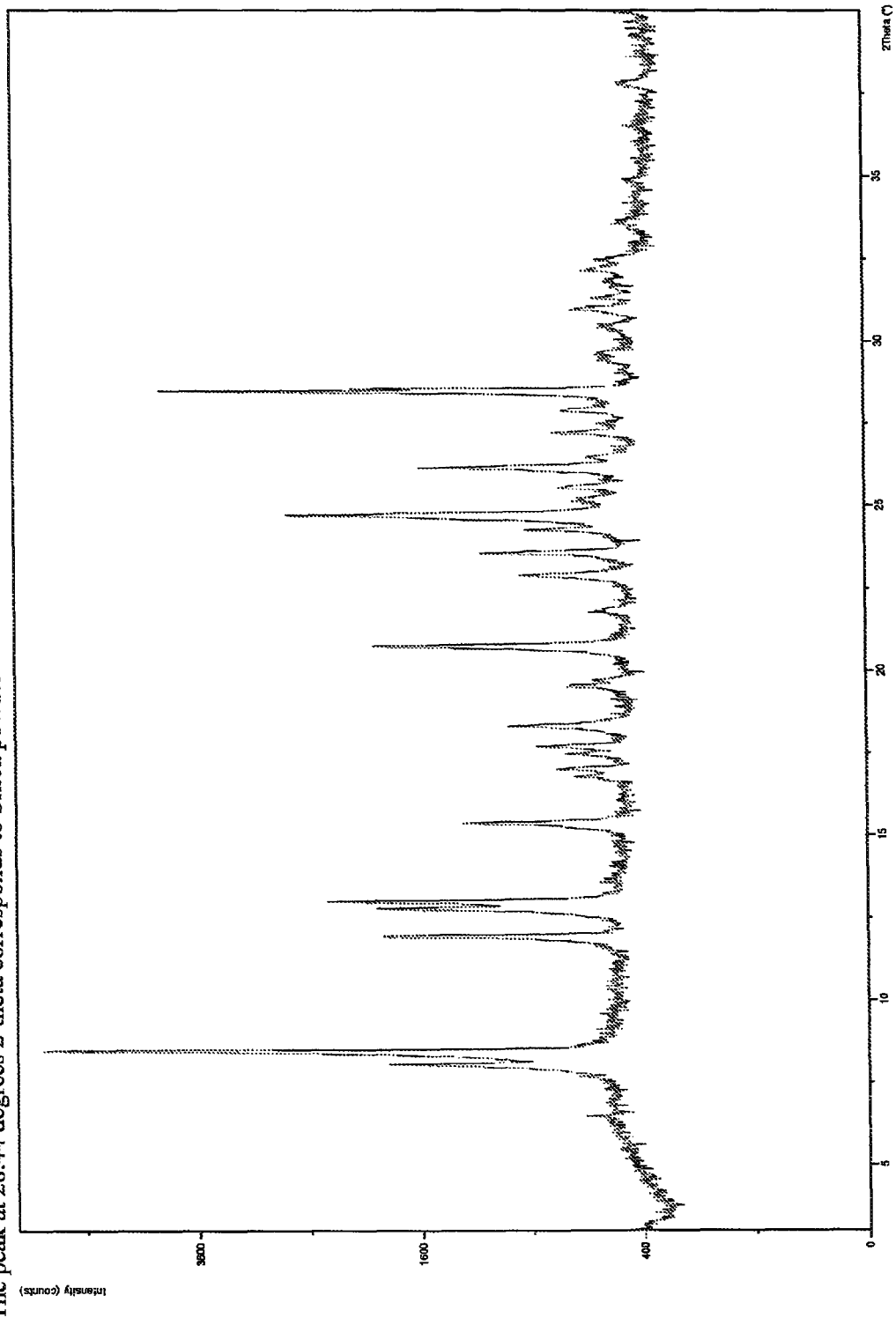
Figure 7: X-ray powder diffraction pattern of form IV of Prasugrel hydrobromide.
* The peak at 28.44 degrees 2-theta corresponds to Silica powder.

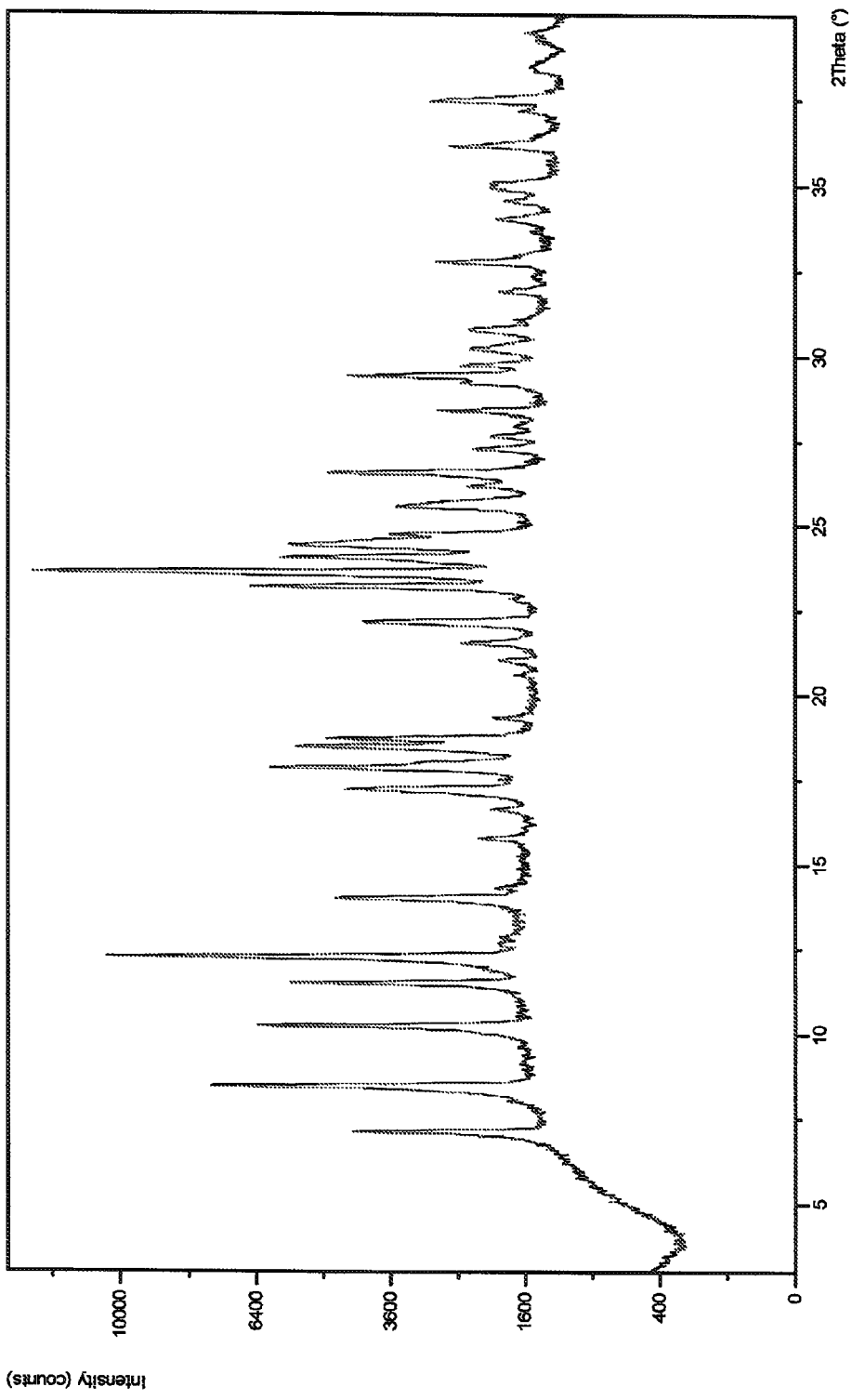
Figure 8: X-ray powder diffraction pattern of form V of Prasugrel hydrobromide.

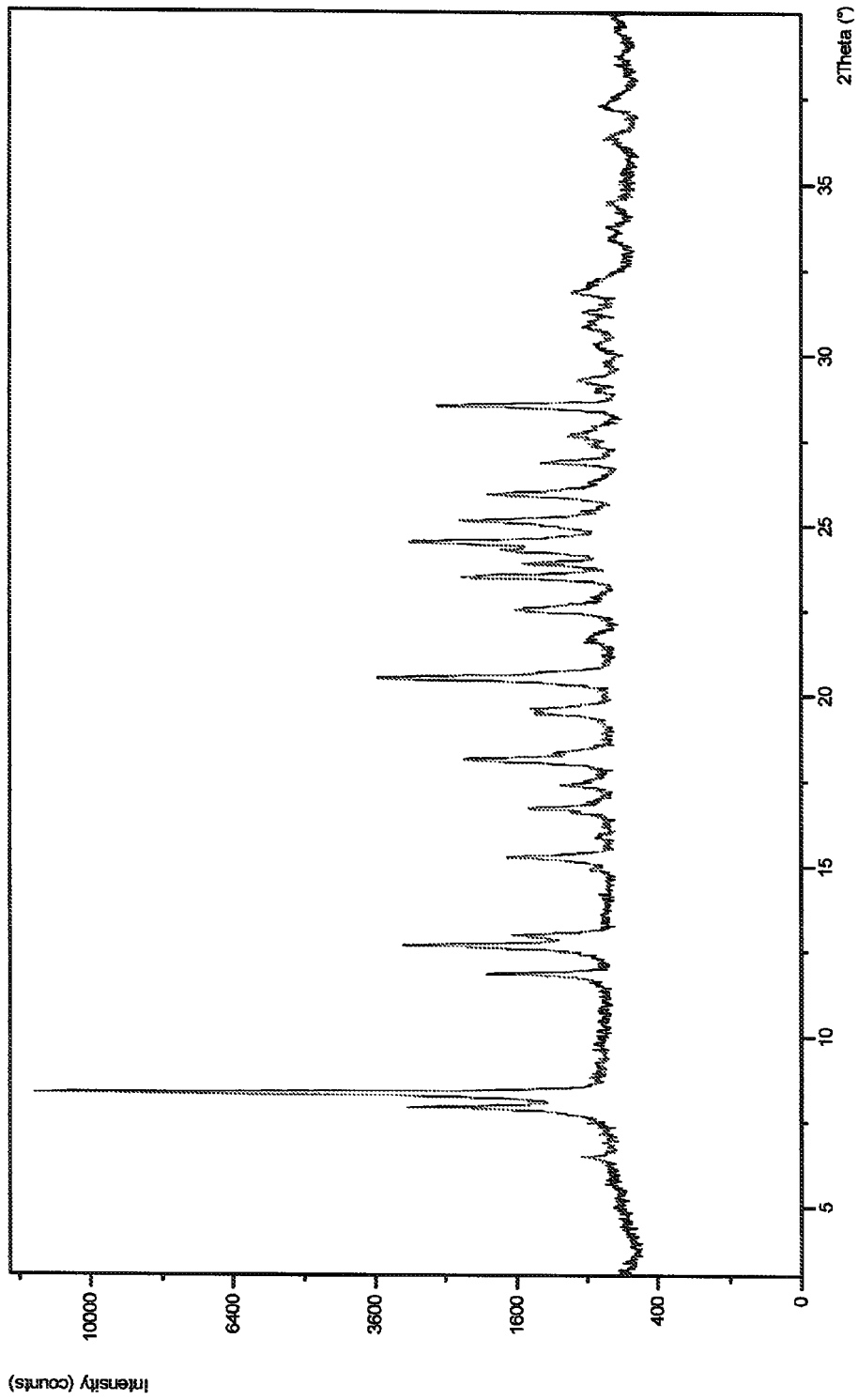
Figure 9: X-ray powder diffraction pattern of form VI of Prasugrel hydrobromide.
* The peak at 28.48 degrees 2-theta corresponds to the silica powder used as an internal standard.

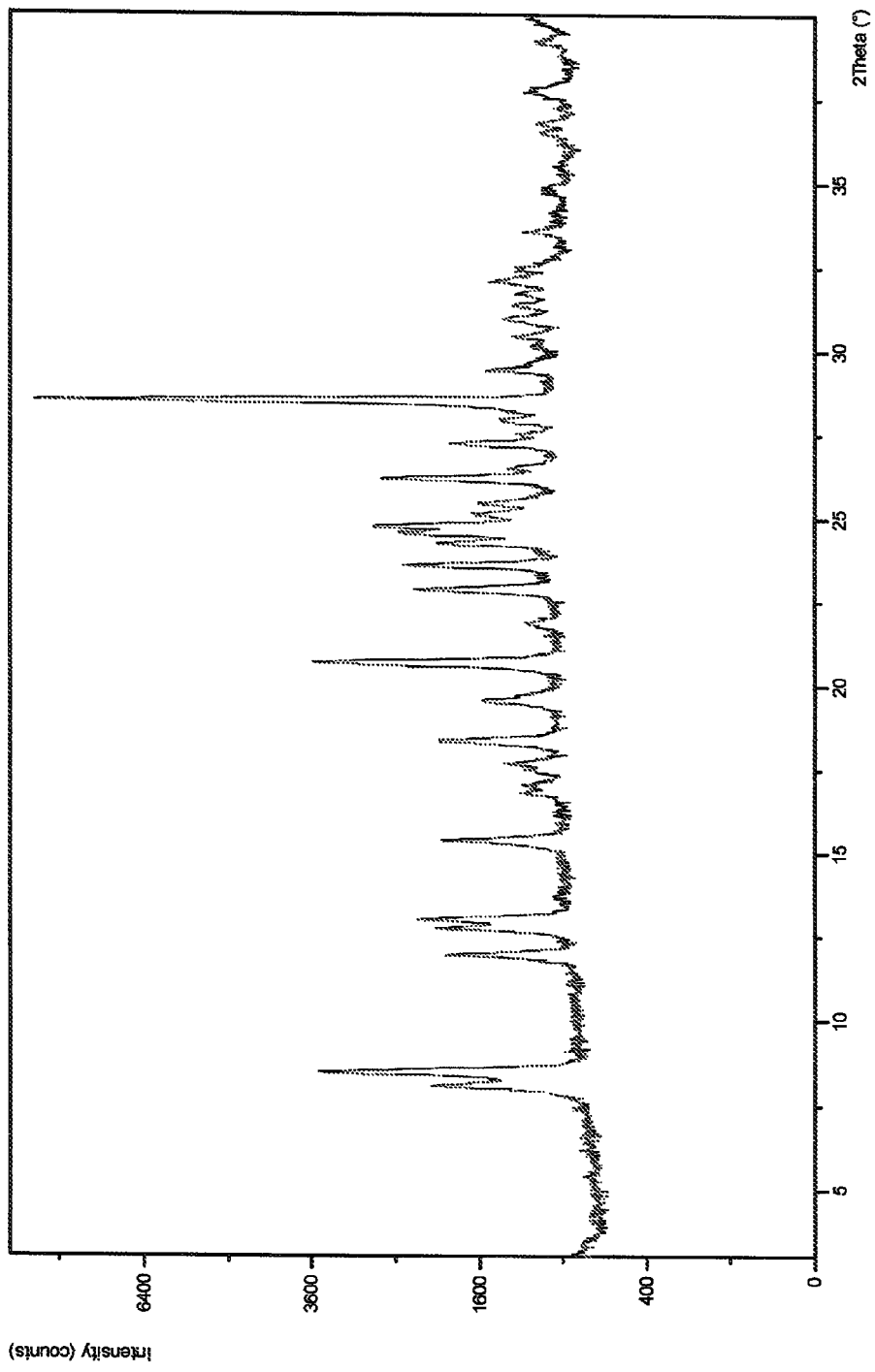
Figure 10: X-ray powder diffraction pattern of form VII of Prasugrel hydrobromide.
* The peak at 28.48 degrees 2-theta corresponds to the silica powder used as an internal standard.

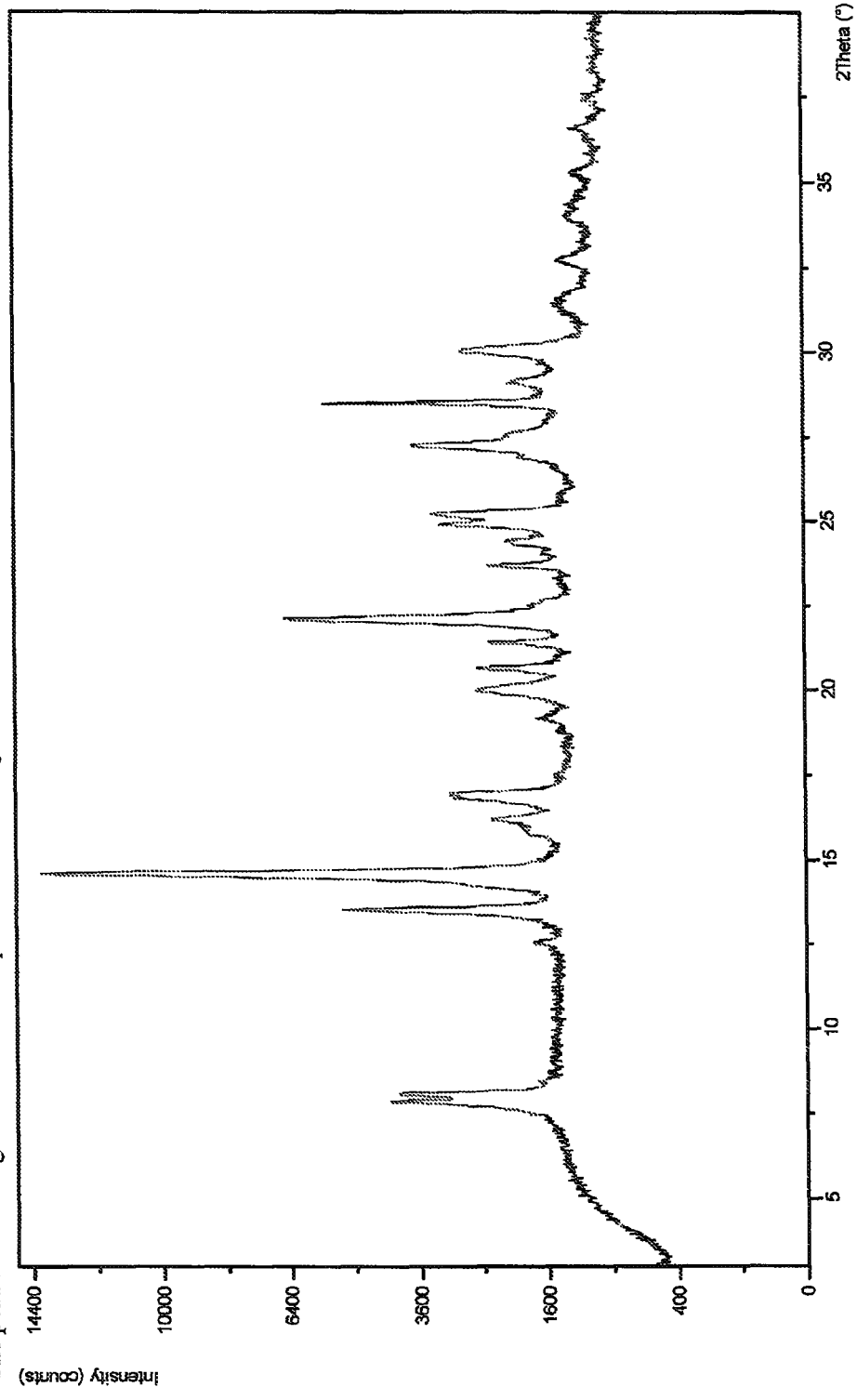
Figure 11: X-ray powder diffraction pattern of form IA of Prasugrel hydrobromide.
* The peak at 28.47 degrees 2-theta corresponds to the silica powder used as an internal standard.

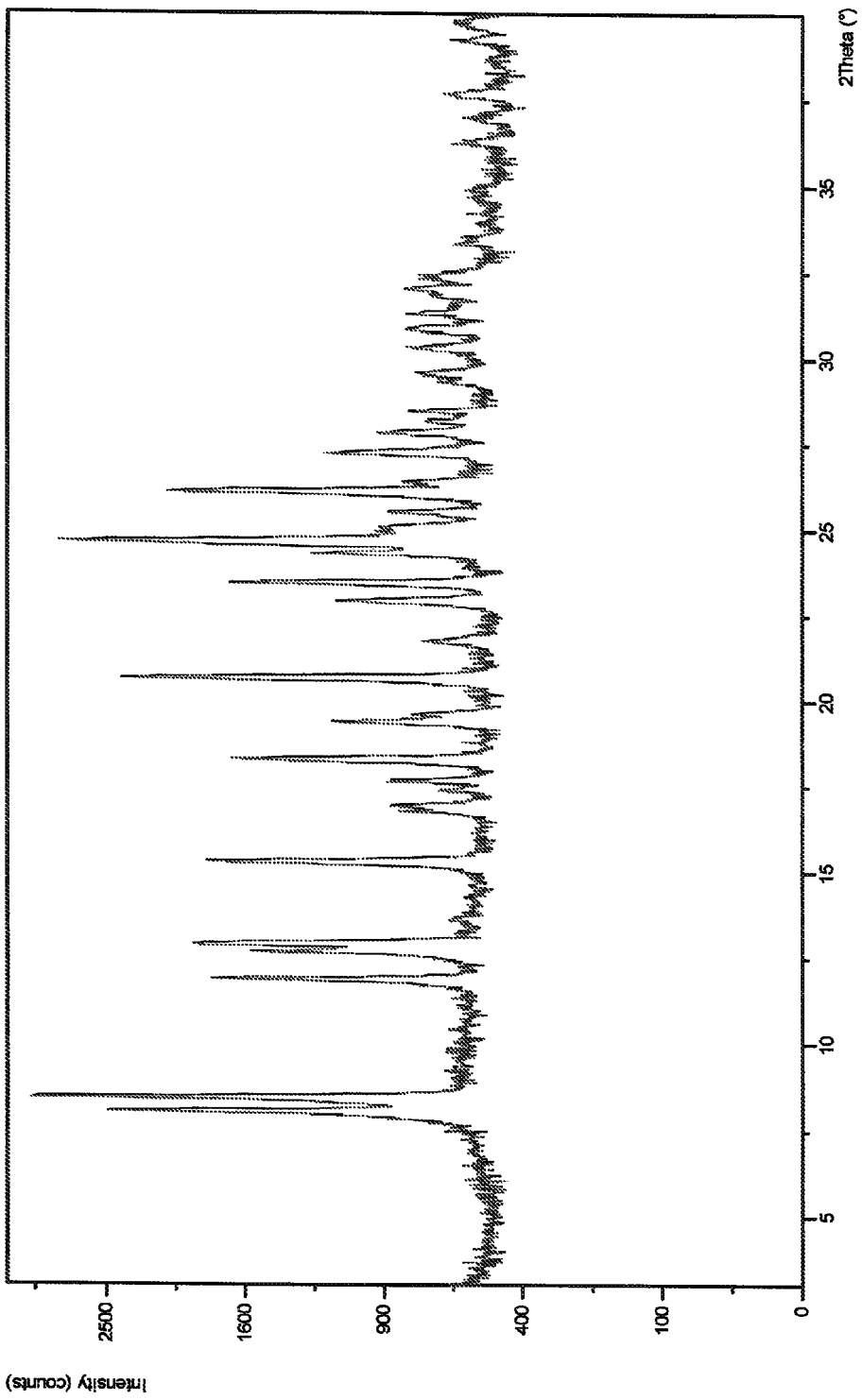
Figure 12: X-ray powder diffraction pattern of form VIII of Prasugrel hydrobromide.
* The peak at 28.44 degrees 2-theta corresponds to the silica powder used as an internal standard.

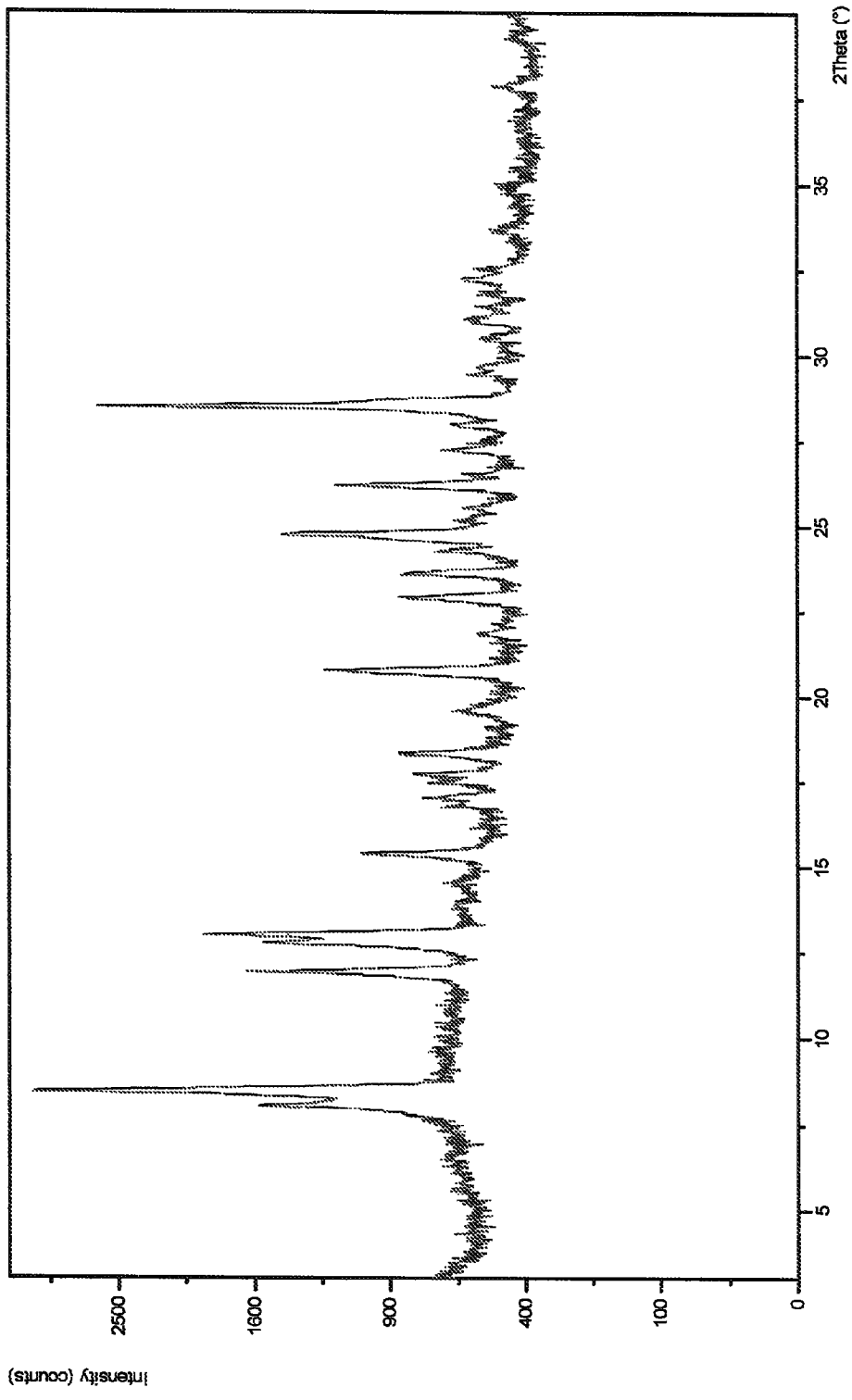
Figure 13: X-ray powder diffraction pattern of form IX of Prasugrel hydrobromide.
* The peak at 28.46 degrees 2-theta corresponds to the silica powder used as an internal standard.

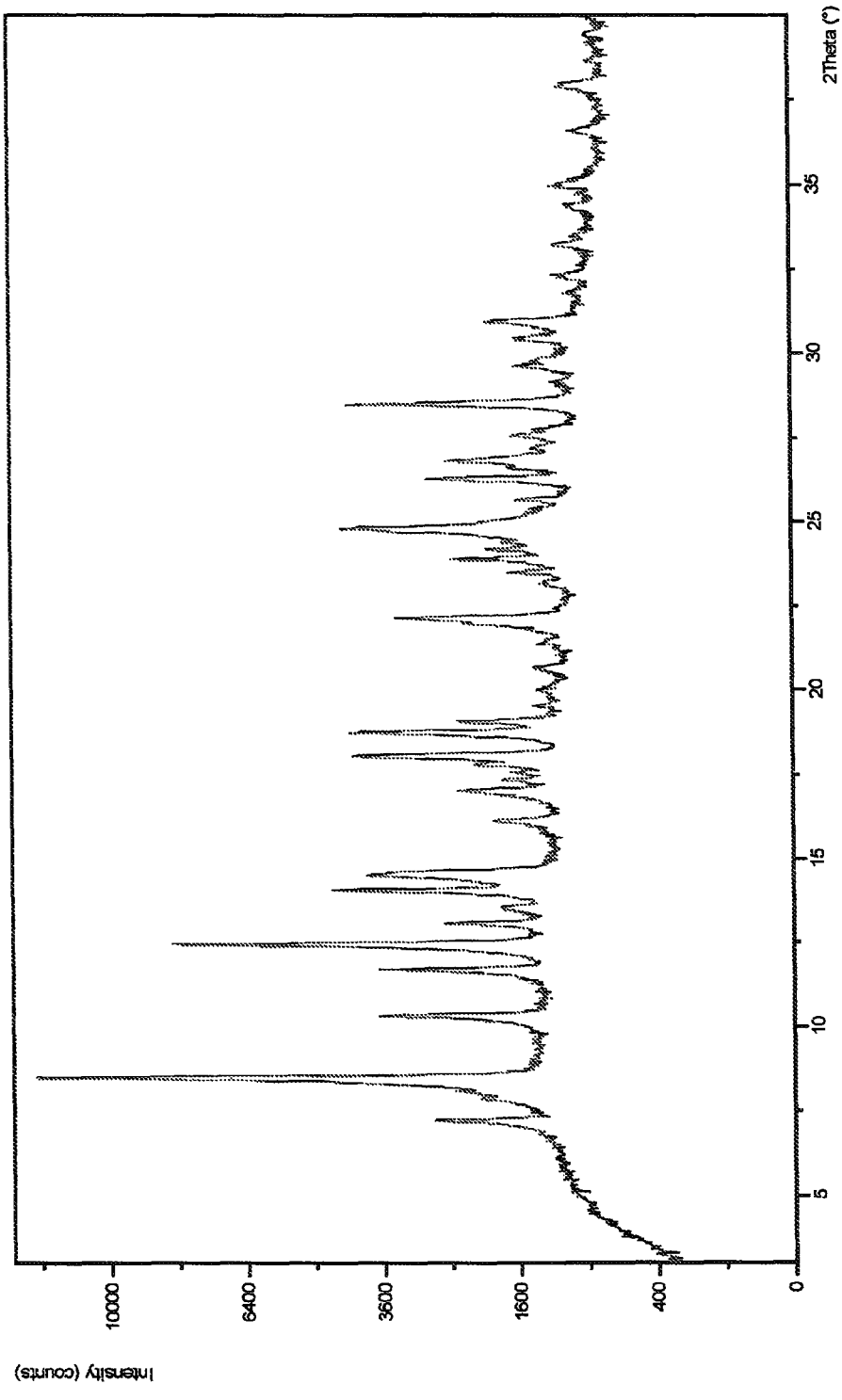
Figure 14: X-ray powder diffraction pattern of form X of Prasugrel hydrobromide.
* The peak at 28.47 degrees 2-theta corresponds to the silica powder used as an internal standard.

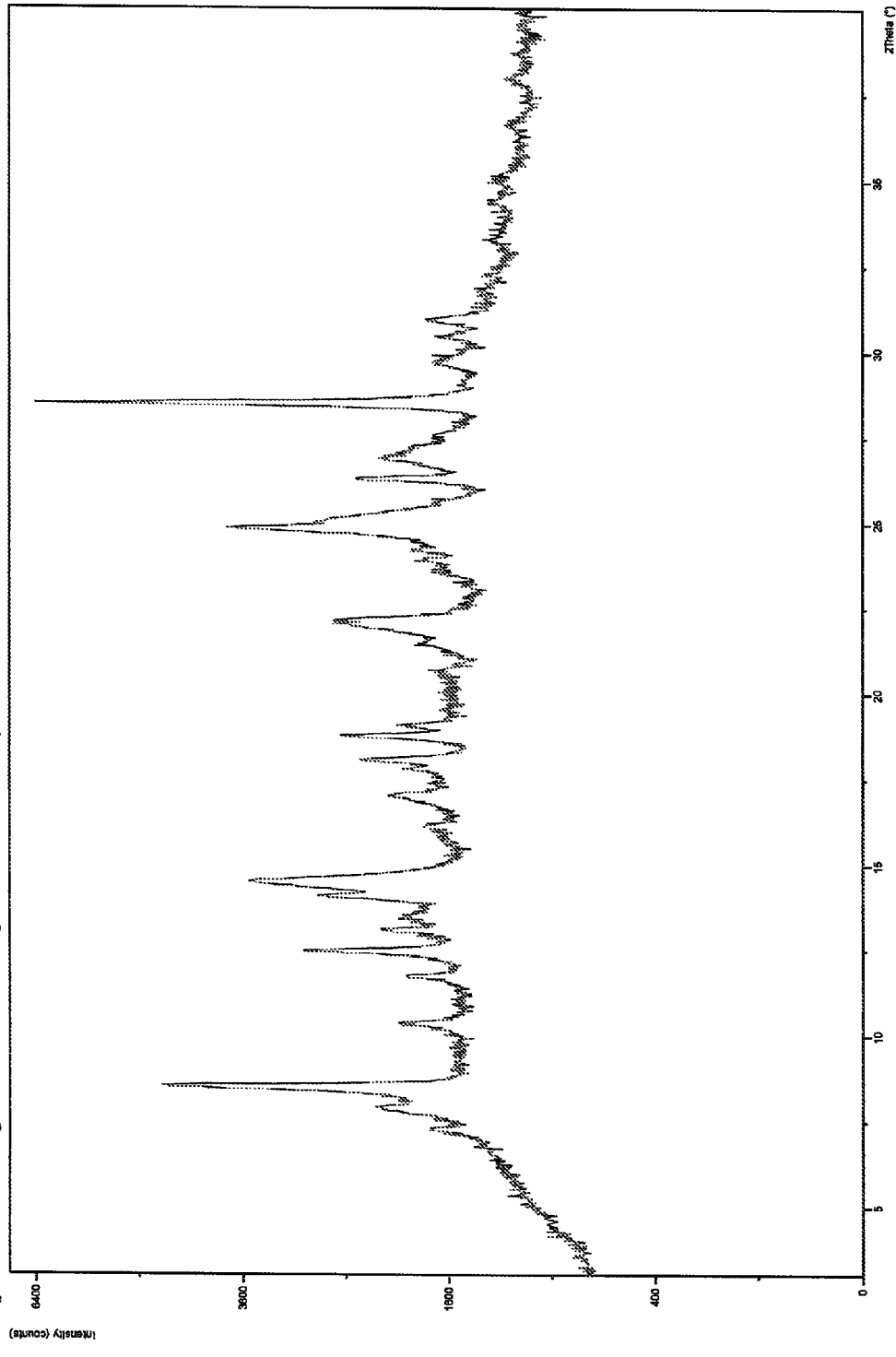
Figure 15: X-ray powder diffraction pattern of form XI of Prasugrel hydrobromide.
* The peak at 28.44 degrees 2-theta corresponds to the silica powder used as an internal standard.

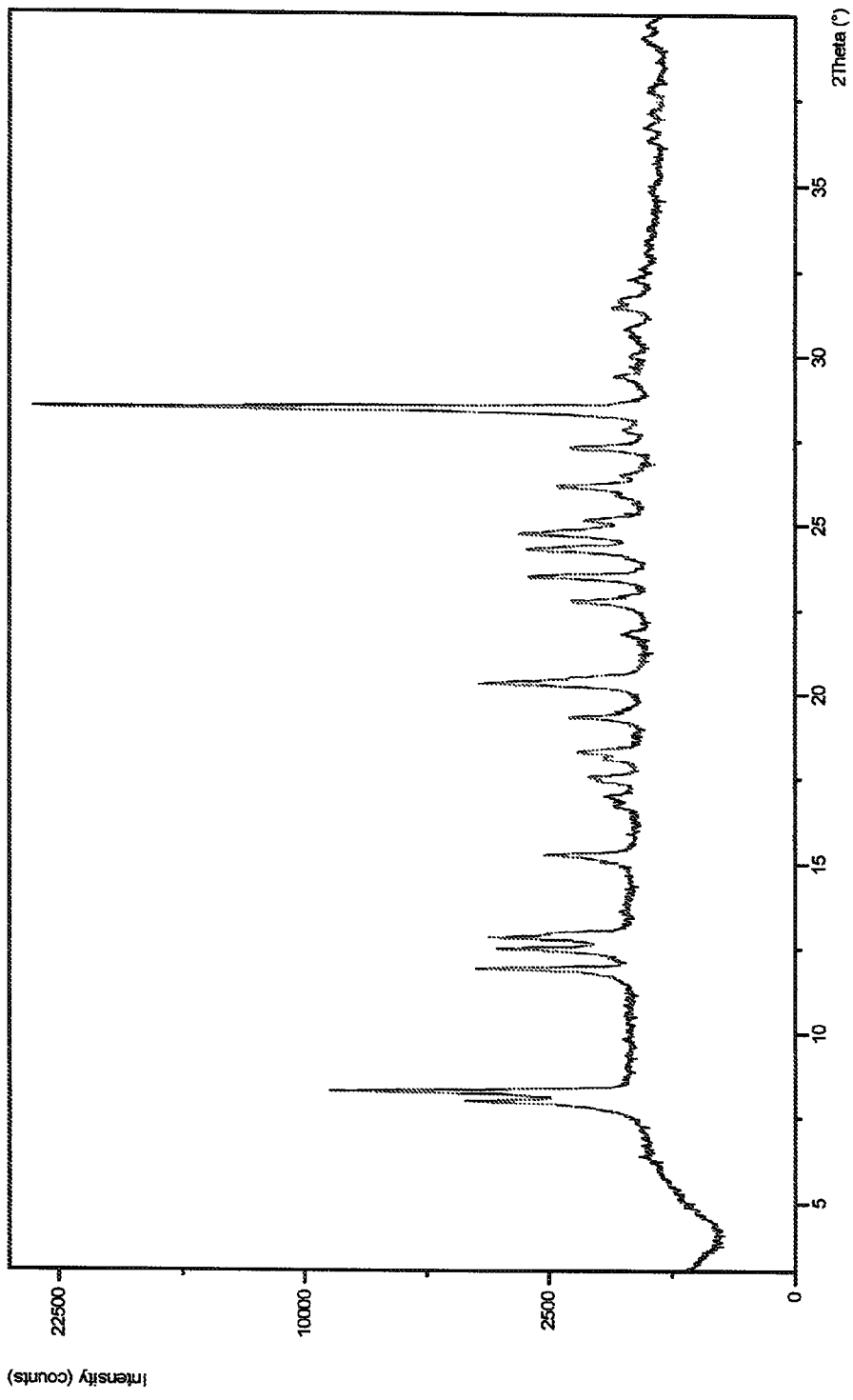
Figure 16: X-ray powder diffraction pattern of form XII of Prasugrel hydrobromide.
* The peak at 28.40 degrees 2-theta corresponds to the silica powder used as an internal standard.

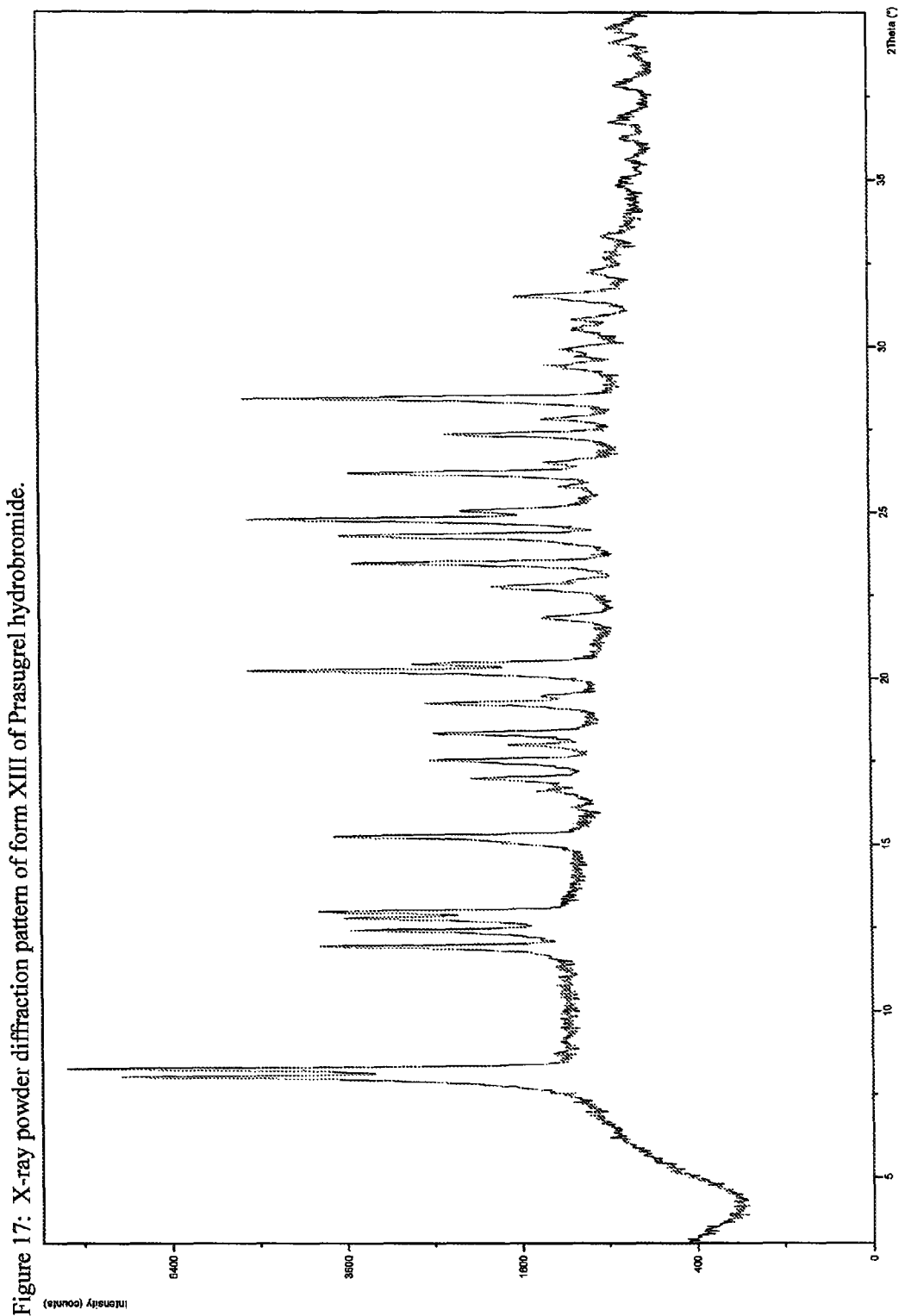
Figure 17: X-ray powder diffraction pattern of form XIII of Prasugrel hydrobromide.

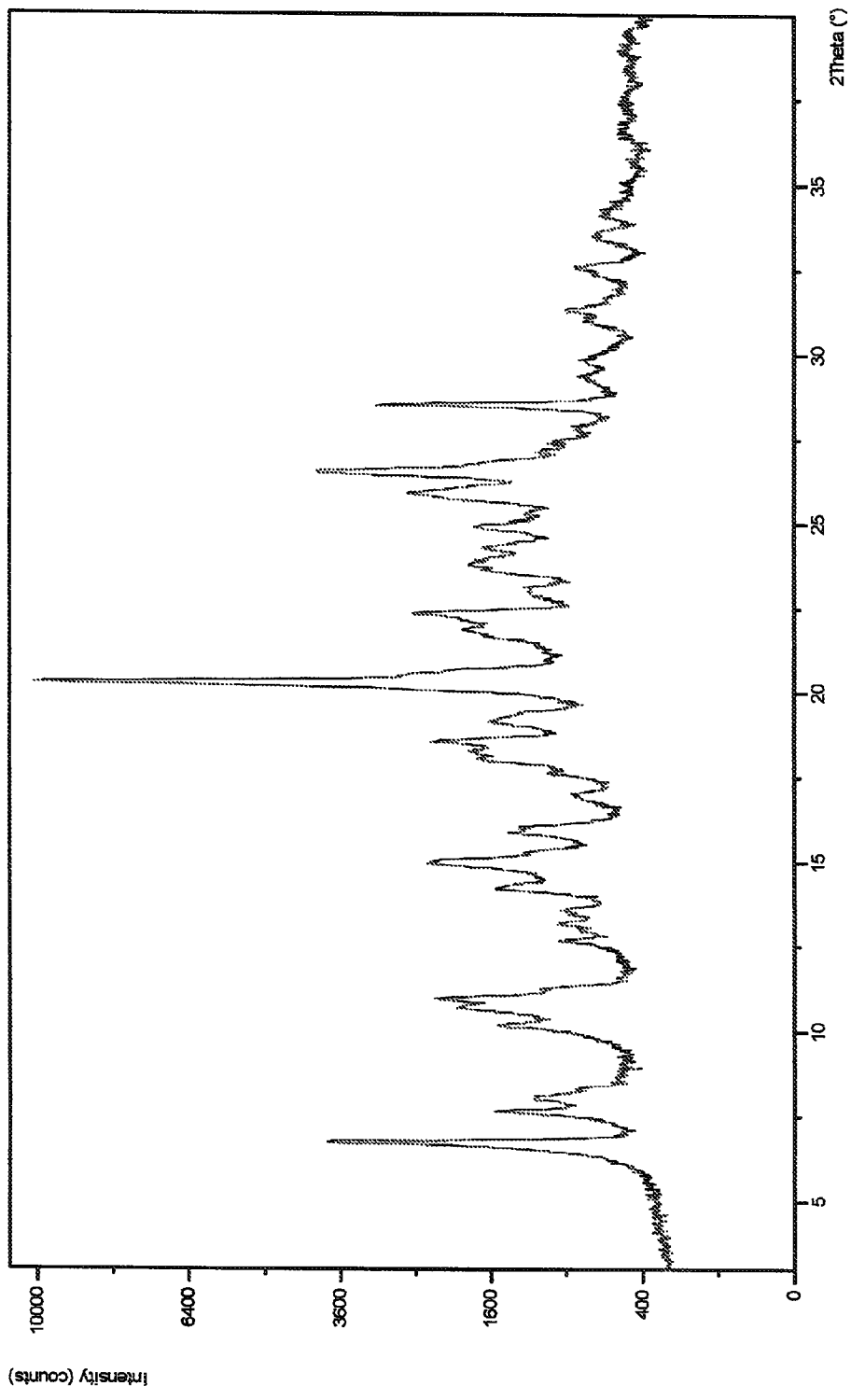
Figure 18: X-ray powder diffraction pattern of form P1 of Prasugrel phosphate.
* The peak at 28.48 degrees 2-theta corresponds to the silica powder used as an internal standard.

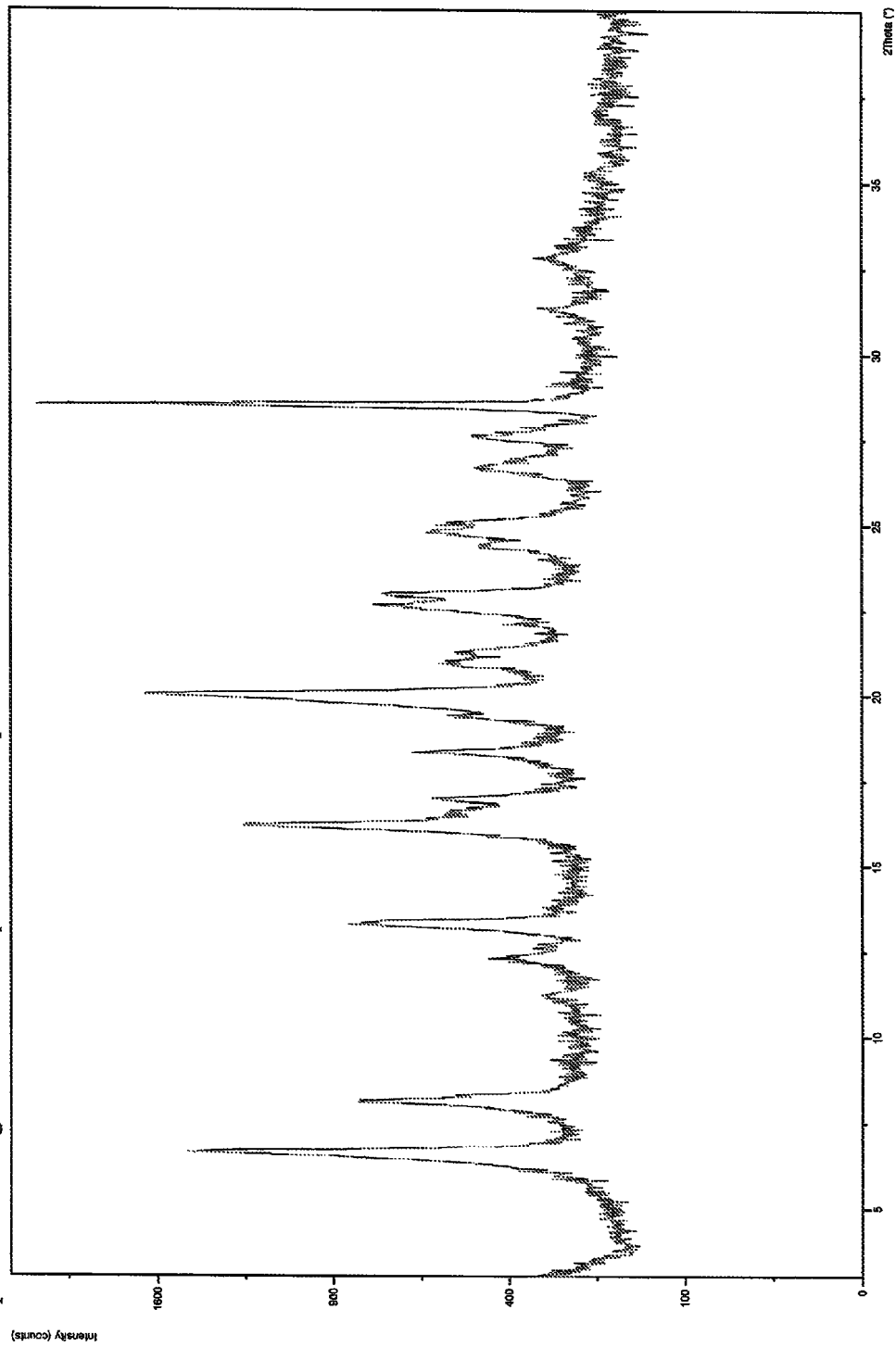
Figure 19: X-ray powder diffraction pattern of form P2 of Prasugrel phosphate.
* The peak at 28.46 degrees 2-theta corresponds to the silica powder used as an internal standard.

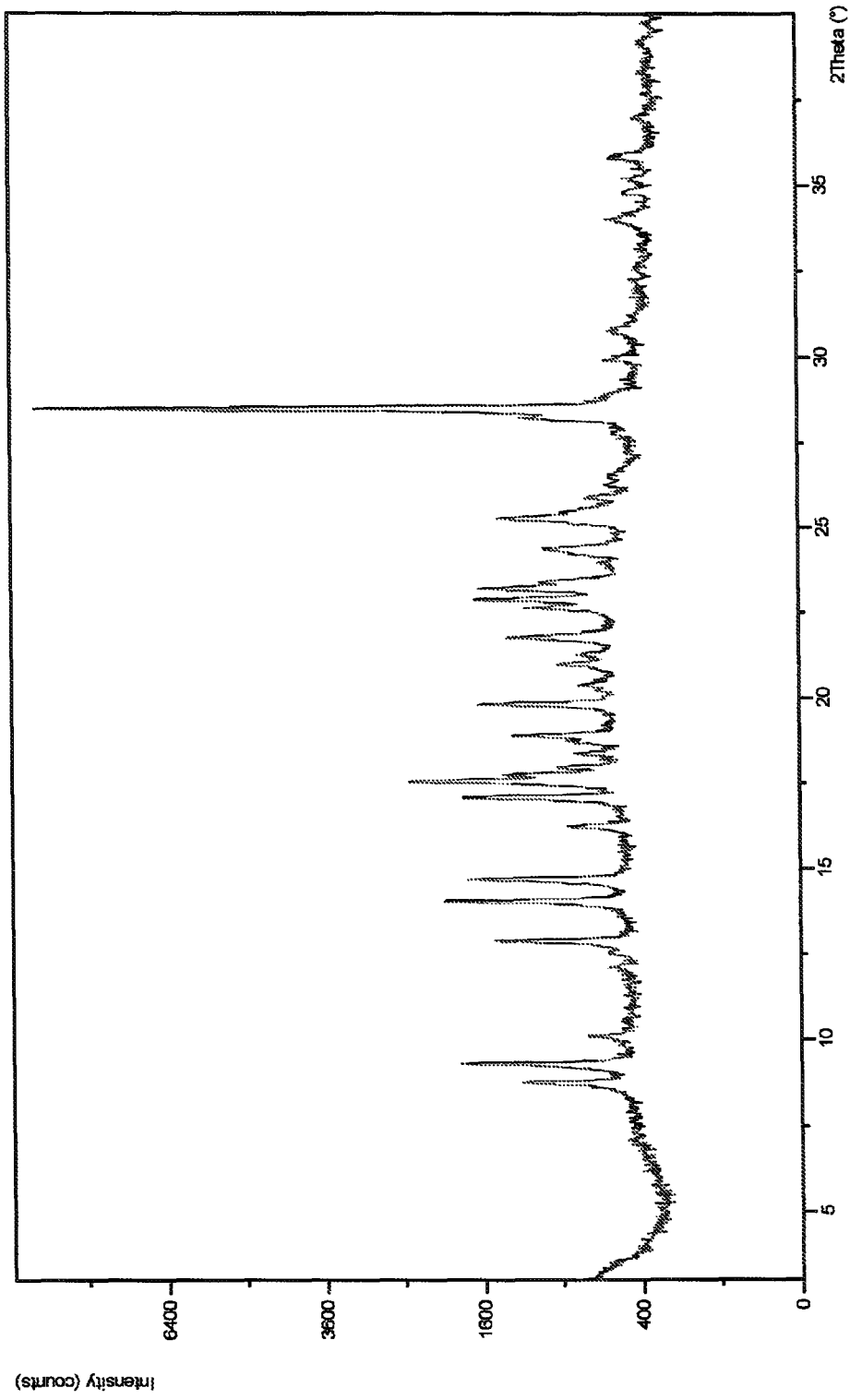
Figure 20: X-ray powder diffraction pattern of form S1 of Prasugrel hydrogensulfate.
* The peak at 28.47 degrees 2-theta corresponds to the silica powder used as an internal standard.

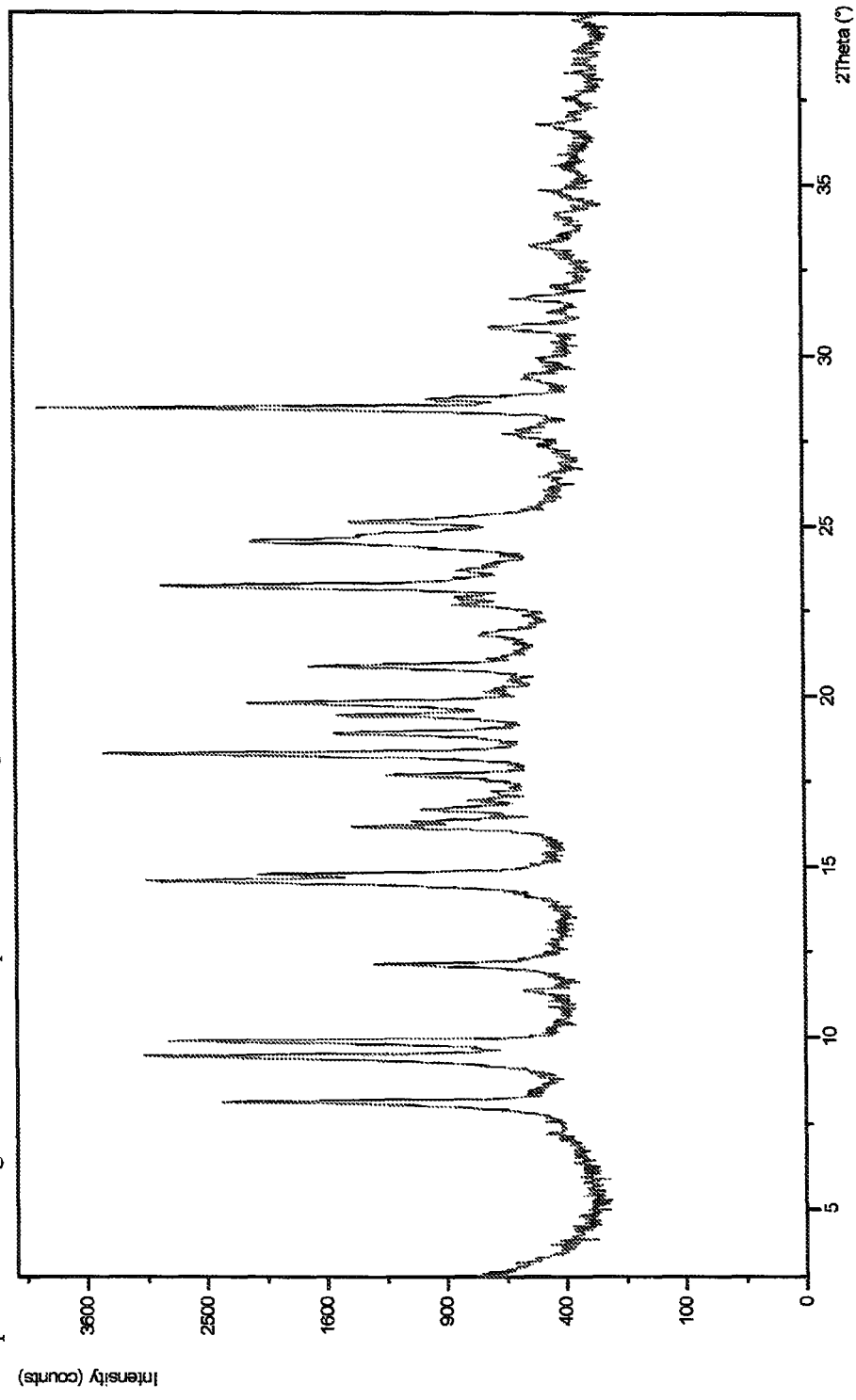
Figure 21: X-ray powder diffraction pattern of form S2 of Prasugrel hydrogensulfate.
* The peak at 28.43 degrees 2-theta corresponds to the silica powder used as an internal standard.

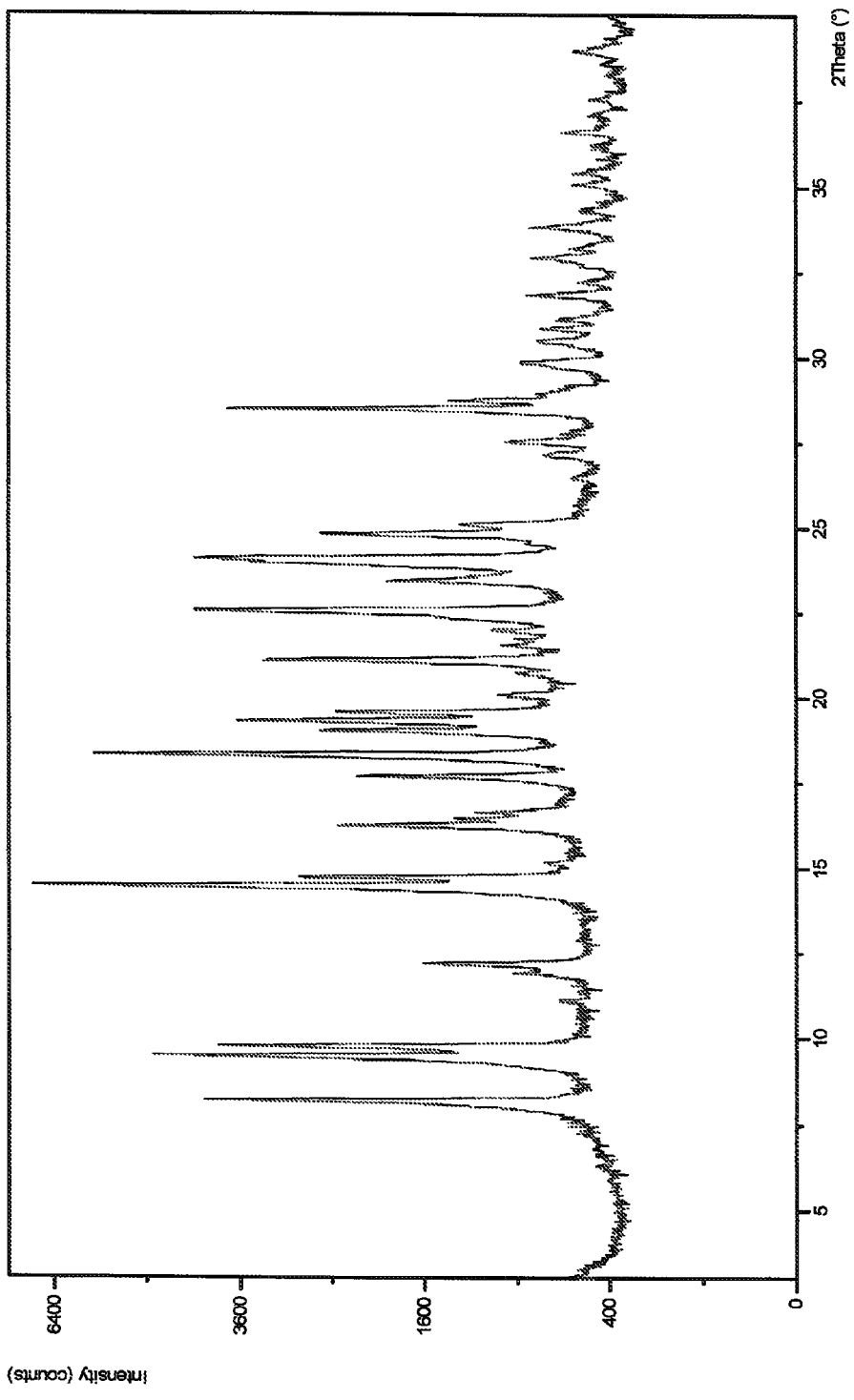
Figure 22: X-ray powder diffraction pattern of form S3 of Prasugrel hydrogensulfate.
* The peak at 28.44 degrees 2-theta corresponds to the silica powder used as an internal standard.

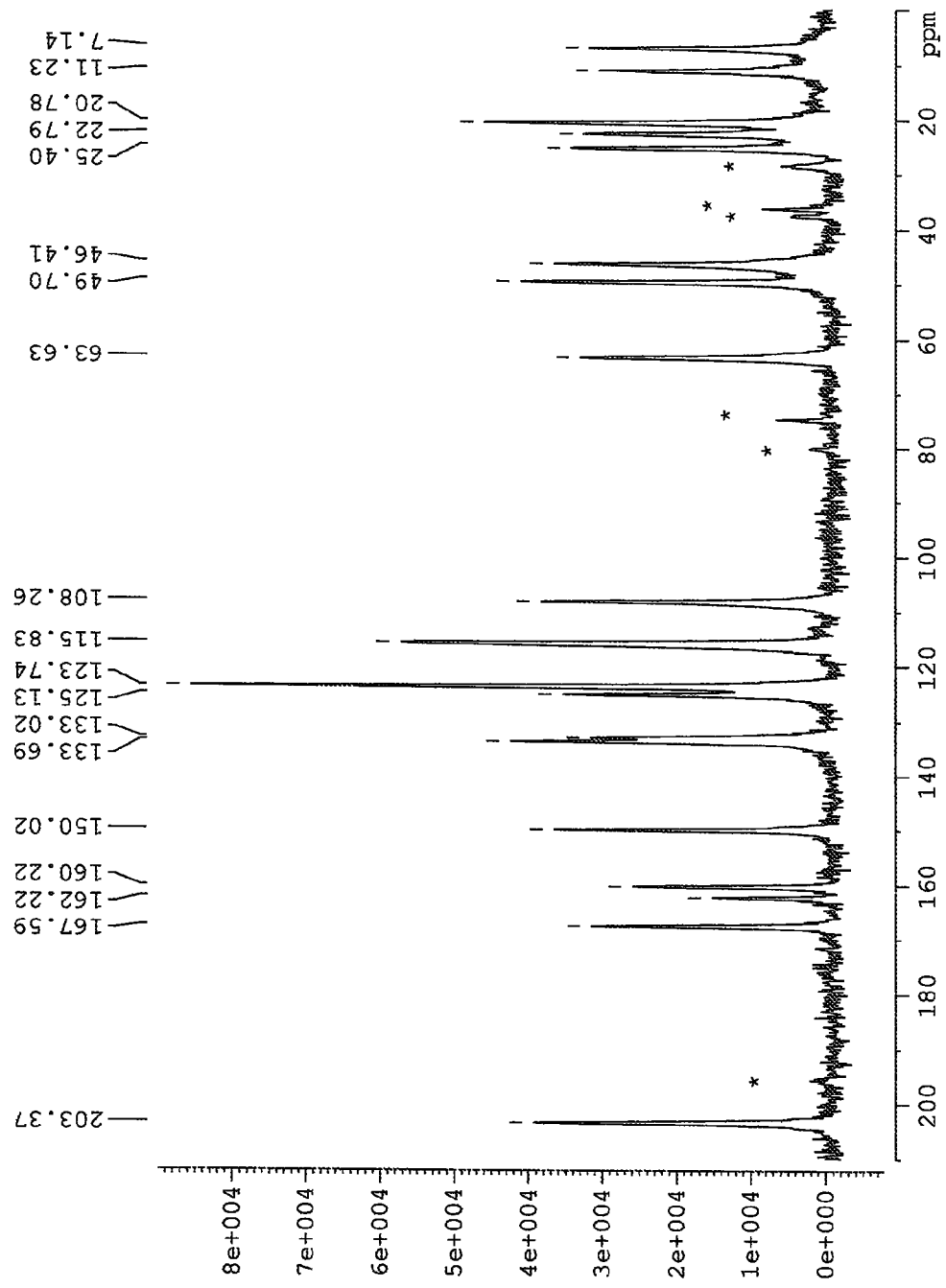
Figure 23: Solid state $^{13}$C NMR spectrum of prasugrel hydrobromide form I.

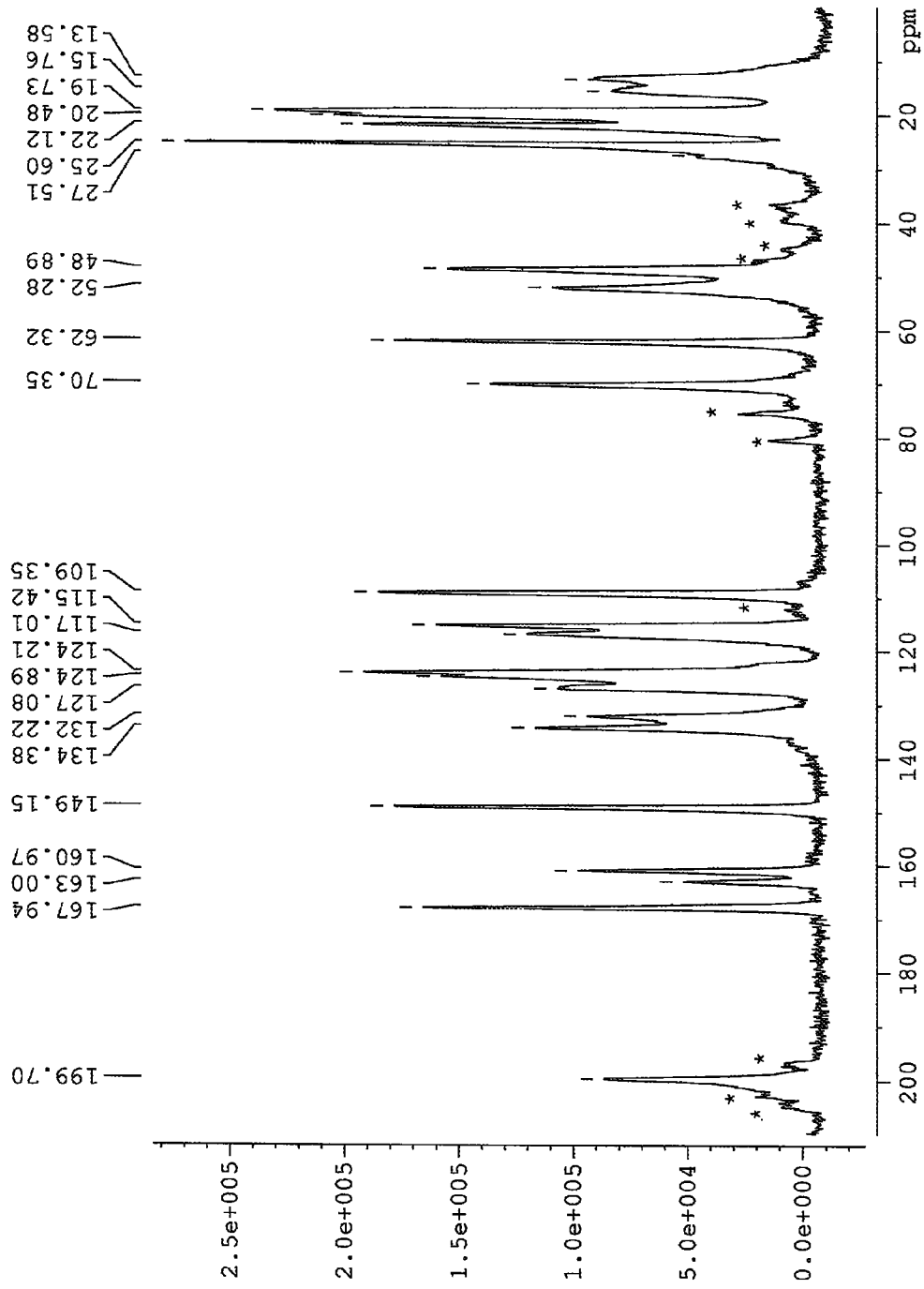
Figure 24: Solid state $^{13}$C NMR spectrum of prasugrel hydrobromide form III.

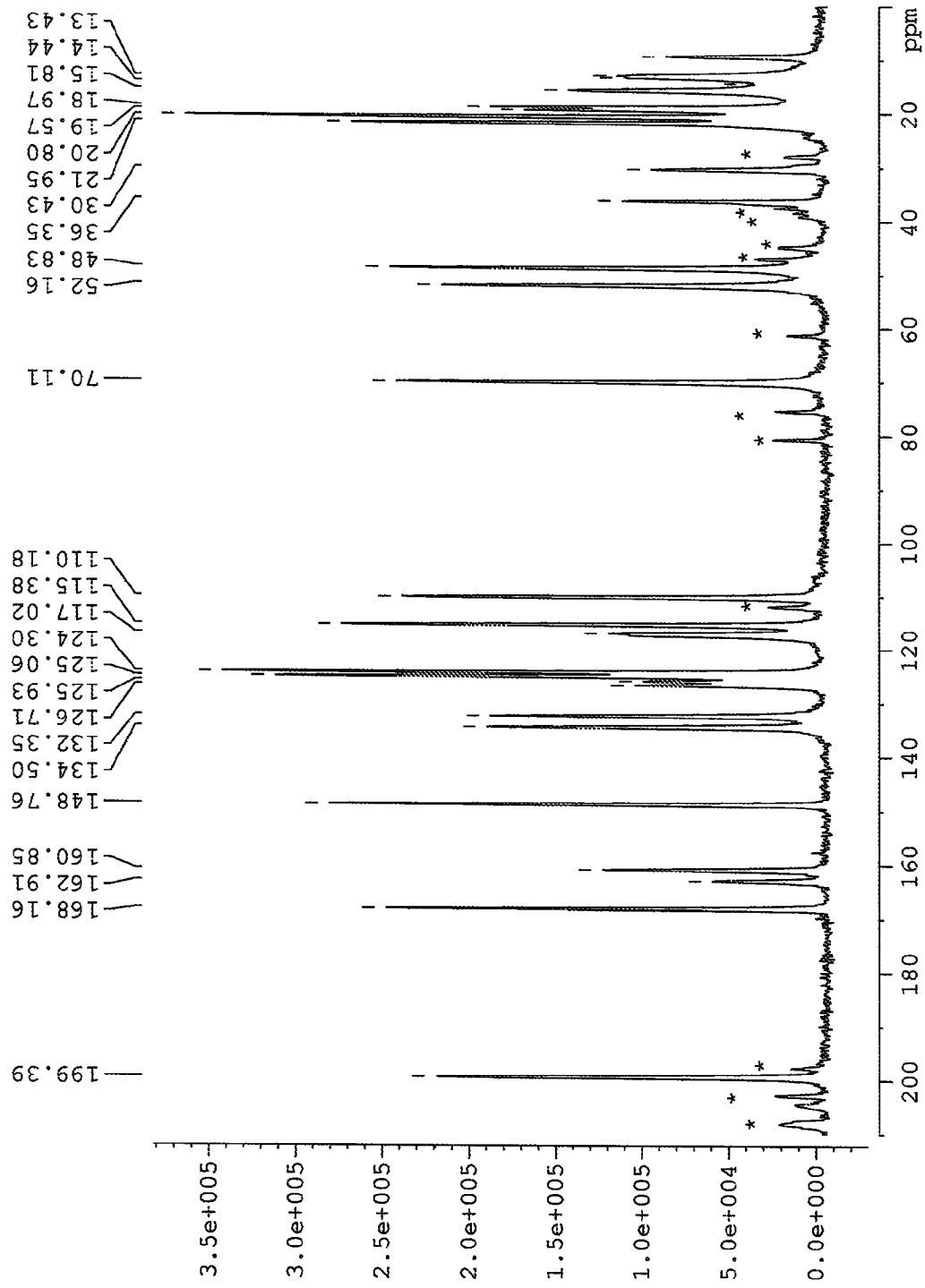
Figure 25: Solid state $^{13}$C NMR spectrum of prasugrel hydrobromide form VII.

CRYSTALLINE FORMS OF PRASUGREL SALTS

CROSS-REFERENCED TO RELATED APPLICATION

This application is a National Stage entry of International Application PCT/US2011/031602, filed Apr. 7, 2011, which claims priority to U.S. Patent Application No. 61/322,165 filed Apr. 8, 2010, U.S. Patent Application 61/326,882 filed Apr. 22, 2010, U.S. Patent Application 61/348,914 filed May 27, 2010, and U.S. Patent Application 61/355,304 filed Jun. 16, 2010, the disclosure of the prior applications are hereby incorporated in their entirety by reference.

FIELD OF THE INVENTION

The present invention relates to Prasugrel salts; solid state forms thereof; the preparation thereof and pharmaceutical compositions thereof.

BACKGROUND OF THE INVENTION

Prasugrel (Formula I) [CAS number: 150322-43-3] has the chemical name 5-(2-cyclopropyl-1-(2-fluorophenyl)-2-oxo-ethyl)-4,5,6,7-tetrahydrothieno[3,2-c]pyridin-2-yl acetate.

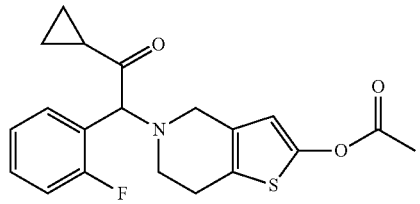

Formula I

Prasugrel is a platelet aggregation inhibitor from the thienopyridine class of ADP (Adenosine diphosphate) receptor inhibitors. These inhibitors reduce the aggregation, or clumping, of platelets by irreversibly binding to $P2Y_{12}$ receptors.

Prasugrel, and salts thereof, in several solid states forms are described in U.S. Pat. No. 5,288,726, U.S. Pat. No. 6,693,115, WO 2007/114526, WO2008/000418, WO2009/062044, CN101255169, WO2010/015144, WO2009/066326, WO2009/098142, WO 2009/129983, WO 2009/130289, CN10/899,056, GB 2469883, WO 2010/070677, WO 2010/111951, WO 2010/094471 and WO 2011/004392.

Polymorphism, the occurrence of different crystal forms, is a property of some molecules and molecular complexes. A single molecule or molecular complex, like Prasugrel hydrochloride, Prasugrel hydrobromide, Prasugrel phosphate, Prasugrel hydrogensulfate or prasugrel nitrate, may give rise to a variety of polymorphs having distinct crystal structures and physical properties like melting point, thermal behaviours (e.g. measured by thermogravimetric analysis—"TGA", or differential scanning calorimetry—"DSC"), x-ray diffraction pattern, e.g., powder x-ray diffraction (PXRD), infrared absorption fingerprint (IR), and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. This also serves to enlarge the repertoire of materials that a formulation scientist has available for formulation optimization, for example by providing a product with different properties, e.g., better processing or handling characteristics, improved dissolution profile, or improved shelf-life. For at least these reasons, there is a need in the art for new polymorphic forms of Prasugrel hydrochloride, Prasugrel hydrobromide, Prasugrel phosphate, Prasugrel hydrogensulfate and prasugrel nitrate.

The present invention provides Prasugrel phosphate, Prasugrel Nitrate; solid state physical properties of Prasugrel hydrochloride, Prasugrel hydrobromide, Prasugrel phosphate, Prasugrel hydrogensulfate and Prasugrel nitrate.

SUMMARY OF THE INVENTION

According to one embodiment the present invention encompasses Prasugrel nitrate and Prasugrel phosphate.

In another embodiment the present invention encompasses crystalline forms of Prasugrel hydrochloride, Prasugrel hydrobromide, Prasugrel phosphate, Prasugrel hydrogensulfate and prasugrel nitrate.

In another embodiment, the present invention encompasses a pharmaceutical composition comprising any of the above described salts and crystalline forms and at least one pharmaceutically acceptable excipient.

In another embodiment, the present invention provides the use of any of the above described salts and crystalline forms for the preparation of formulations.

In another embodiment, the present invention encompasses the use of any of the above described salts and crystalline forms for the preparation Prasugrel hydrochloride.

In another embodiment, the present invention provides the use of any of the above pharmaceutical compositions for reducing the aggregation ("clumping") of platelets.

BRIEF DESCRIPTION OF THE DRAWINGS

FIG. 1 shows an X-ray powder diffraction pattern for crystalline Prasugrel hydrochloride nitromethane solvate.

FIG. 2 shows an X-ray powder diffraction pattern for crystalline Prasugrel hydrochloride Form F.

FIG. 3 shows an X-ray powder diffraction pattern for crystalline Prasugrel nitrate.

FIG. 4 shows an X-ray powder diffraction pattern for crystalline Prasugrel hydrobromide Form II.

FIG. 5 shows an X-ray powder diffraction pattern for crystalline Prasugrel hydrobromide Form III.

FIG. 6 shows an X-ray powder diffraction pattern for crystalline Prasugrel hydrobromide Form I.

FIG. 7 shows an X-ray powder diffraction pattern for crystalline Prasugrel hydrobromide Form IV.

FIG. 8 shows an X-ray powder diffraction pattern for crystalline Prasugrel hydrobromide Form V.

FIG. 9 shows an X-ray powder diffraction pattern for crystalline Prasugrel hydrobromide Form VI.

FIG. 10 shows an X-ray powder diffraction pattern for crystalline Prasugrel hydrobromide Form VII.

FIG. 11 shows an X-ray powder diffraction pattern for crystalline Prasugrel hydrobromide Form IA.

FIG. 12 shows an X-ray powder diffraction pattern for crystalline Prasugrel hydrobromide Form Viii.

FIG. 13 shows an X-ray powder diffraction pattern for crystalline Prasugrel hydrobromide Form IX.

FIG. 14 shows an X-ray powder diffraction pattern for crystalline Prasugrel hydrobromide Form X.

FIG. 15 shows an X-ray powder diffraction pattern for crystalline Prasugrel hydrobromide Form XI.

FIG. 16 shows an X-ray powder diffraction pattern for crystalline Prasugrel hydrobromide Form XII.

FIG. 17 shows an X-ray powder diffraction pattern for crystalline Prasugrel hydrobromide Form XIII.

FIG. 18 shows an X-ray powder diffraction pattern for crystalline Prasugrel phosphate Form P1.

FIG. 19 shows an X-ray powder diffraction pattern for crystalline Prasugrel phosphate Form P2.

FIG. 20 shows an X-ray powder diffraction pattern for crystalline Prasugrel hydrogen sulfate Form S1.

FIG. 21 shows an X-ray powder diffraction pattern for crystalline Prasugrel hydrogen sulfate Form S2.

FIG. 22 shows an X-ray powder diffraction pattern for crystalline Prasugrel hydrogen sulfate Form S3.

FIG. 23 shows a solid state $^{13}$C NMR spectrum of crystalline Prasugrel hydrobromide Form I.

FIG. 24 shows a solid state $^{13}$C NMR spectrum of crystalline Prasugrel hydrobromide Form III.

FIG. 25 shows a solid state $^{13}$C NMR spectrum of crystalline Prasugrel hydrobromide Form VII.

DETAILED DESCRIPTION

As used herein, the term "Room temperature" refers to a temperature between about 20° C. and about 30° C. Usually, room temperature ranges from about 20° C. to about 25° C.

As used herein, the term "Overnight" refers to a period of between about 15 and about 20 hours, typically between about 16 to about 20 hours.

As used herein, and unless stated otherwise, the term "anhydrous" in relation to crystalline Prasugrel hydrobromide form I and IA relates to a crystalline Prasugrel hydrobromide form I and IA which contains not more than 1% (w/w) of either water or organic solvents as measured by TGA.

A crystal form may be referred to herein as being characterized by graphical data substantially "as depicted in" a Figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

Crystalline forms of Prasugrel hydrochloride, Prasugrel hydrobromide, Prasugrel phosphate, Prasugrel hydrogensulfate and prasugrel nitrate have advantageous properties selected from at least one of: chemical purity, flowability, solubility, morphology or crystal habit, stability—such as storage stability, stability to dehydration, stability to polymorphic conversion, low hygroscopicity, and low content of residual solvents.

Crystalline Forms I and IA of Prasugrel hydrobromide described herein are advantageous as active agents or as starting materials for the preparation of other salts of prasugrel. In particular, the crystalline Forms I and IA have advantageous properties compared with other prasugrel forms. For example, Forms I and IA of prasugrel hydrobromide show stability, e.g. with respect to chemical degradation, compared to, for example, prasugrel hydrochloride.

In any embodiment of the present invention, by "substantially free" is meant that the forms of the present invention contain 20% (w/w) or less, 10% (w/w) or less, 5% (w/w) or less, 2% (w/w) or less, particularly 1% (w/w) or less, more particularly 0.5% (w/w) or less, and most particularly 0.2% (w/w) or less of either any other polymorphs, or of a specified polymorph of Prasugrel. In other embodiments, the polymorphs of Prasugrel salts of the invention contain from 1% to 20% (w/w), from 5% to 20% (w/w), or from 5% to 10% (w/w) of any other polymorphs or of a specified polymorph of Prasugrel.

The present invention addresses a need in the art by providing salts and crystalline forms of prasugrel, specifically prasugrel hydrochloride, prasugrel hydrobromide, Prasugrel phosphate, Prasugrel hydrogensulfate and prasugrel nitrate that have advantageous properties selected from at least one of: flowability, solubility, morphology or crystal habit, stability—such as storage stability, stability to dehydration, stability to polymorphic conversion—and low hygroscopicity.

In one embodiment, the present invention provides Prasugrel nitrate and Prasugrel phosphate.

In one embodiment, the present invention provides Prasugrel hydrochloride nitromethane solvate. Preferably, the Prasugrel hydrochloride nitromethane solvate is solid, more preferably, a crystalline solid.

In another embodiment, the present invention provides a crystalline form of Prasugrel hydrochloride nitromethane solvate, characterized by data selected from: an X-ray powder diffraction pattern having peaks at 8.4, 10.2, 13.8, 21.7 and 23.8 degrees two theta±0.2 degrees two theta; an XRPD pattern substantially as depicted in FIG. 1; and combinations thereof. The crystalline form of Prasugrel hydrochloride nitromethane solvate can be further characterized by an X-ray powder diffraction pattern having additional peaks at 11.7, 12.4, 16.7, 17.7 and 26.6 degrees two theta±0.2 degrees two theta.

In one embodiment, the present invention provides a crystalline form of Prasugrel hydrochloride, designated as Form F. Form F can be characterized by data selected from: an X-ray powder diffraction pattern having peaks at 10.3, 11.6, 12.4, 14.0 and 23.7 degrees two theta±0.2 degrees two theta; an XRPD pattern substantially as depicted in FIG. 2; and combinations thereof. The crystalline Prasugrel hydrochloride acetic acid solvate, Form F can be further characterized by a powder XRD pattern having additional peaks at 8.5, 16.0, 18.6, 18.9 and 23.3 degrees two theta±0.2 degrees two theta. Preferably, form F of prasugrel hydrochloride can be an acetic acid solvate.

The present invention provides Prasugrel nitrate. Preferably, the Prasugrel nitrate is solid, more preferably, a crystalline solid.

The present invention further provides a crystalline form of Prasugrel nitrate, characterized by data selected from: an X-ray powder diffraction pattern having peaks at 8.3, 9.3, 12.2, 19.2 and 23.5 degrees two theta±0.2 degrees two theta; an XRPD pattern substantially as depicted in FIG. 3; and combinations thereof. The crystalline form of Prasugrel nitrate can be further characterized by an X-ray powder diffraction pattern having additional peaks at 9.1, 18.1, 20.2, 24.7 and 25.2 degrees two theta±0.2 degrees two theta. Preferably, the crystalline form of prasugrel nitrate can be an acetone solvate.

The present invention provides a crystalline form of Prasugrel hydrobromide, designated as Form II. Form II can be characterized by data selected from: an X-ray powder diffraction pattern having peaks at 7.1, 8.3, 10.1, 13.8 and 21.7 degrees two theta±0.2 degrees two theta; an XRPD pattern substantially as depicted in FIG. 4; and combinations thereof. Crystalline Form II can be further characterized by a powder XRD pattern having additional peaks at 12.2, 17.6, 18.4, 24.2 and 25.9 degrees two theta±0.2 degrees two theta. Preferably, crystalline Form II of prasugrel hydrobromide can be an acetone solvate.

The present invention provides a crystalline form of Prasugrel hydrobromide, designated as Form III. Form III can be characterized by data selected from: an X-ray powder diffraction pattern having peaks at 8.0, 8.4, 12.6, 18.2 and 20.5 degrees two theta±0.2 degrees two theta; an XRPD pattern substantially as depicted in FIG. 5; a solid-state $^{13}C$ NMR spectrum having peaks at 52.3, 70.4, 124.2, 149.2 and 199.7±0.2 ppm; a solid-state $^{13}C$ NMR spectrum substantially as depicted in FIG. 24 and combinations thereof. Crystalline Form III can be further characterized by a powder XRD pattern having additional peaks at 6.5, 11.9, 15.2, 23.4 and 24.5 degrees two theta±0.2 degrees two theta. Preferably, crystalline form III of prasugrel hydrobromide can be a 2-propanol solvate.

The present invention provides a crystalline form of Prasugrel hydrobromide, designated as Form I. Form I can be characterized by data selected from an X-ray powder diffraction pattern having additional peaks at 7.8, 14.4, 16.9, 22.0 and 25.1 degrees two theta±0.2 degrees two theta; an XRPD pattern substantially as depicted in FIG. 6; a solid-state $^{13}C$ NMR spectrum having peaks at 7.1, 11.2, 63.6, 123.7 and 203.4±0.2 ppm; a solid-state $^{13}C$ NMR spectrum substantially as depicted in FIG. 23 and combinations thereof. Form I can be further characterized by a powder XRD pattern having additional peaks at 13.5, 19.9, 23.6, 27.0 and 29.7 degrees two theta±0.2 degrees two theta. Preferably, crystalline Form I of prasugrel hydrobromide can be anhydrous.

The present invention provides a crystalline form of Prasugrel hydrobromide, designated as Form IV. Form IV can be characterized by data selected from: an X-ray powder diffraction pattern having peaks at 8.5, 12.8, 13.0, 20.7 and 24.7 degrees two theta±0.2 degrees two theta; an XRPD pattern substantially as depicted in FIG. 7; and combinations thereof. Form IV can be further characterized by a powder XRD pattern having additional peaks at 8.0, 18.3, 22.9, 26.1 and 27.2 degrees two theta±0.2 degrees two theta. Preferably, crystalline form IV of prasugrel hydrobromide can be an ethanol solvate.

The present invention provides a crystalline form of Prasugrel hydrobromide, designated as Form V. Form V can be characterized by data selected from: an X-ray powder diffraction pattern having peaks at 7.1, 8.5, 17.2, 17.8 and 23.5 degrees two theta±0.2 degrees two theta; an XRPD pattern substantially as depicted in FIG. 8; and combinations thereof. Form V can be further characterized by a powder XRD pattern having additional peaks at 10.2, 11.5, 12.3, 18.4 and 23.1 degrees two theta±0.2 degrees two theta. Preferably, crystalline form V of prasugrel hydrobromide can be an acetic acid solvate.

The present invention provides a crystalline form of Prasugrel hydrobromide, designated as Form VI. Form VI can be characterized by data selected from: an X-ray powder diffraction pattern having peaks at 7.9, 8.3, 11.8, 18.1 and 20.4 degrees two theta±0.2 degrees two theta; an XRPD pattern substantially as depicted in FIG. 9; and combinations thereof. Form VI can be further characterized by a powder XRD pattern having additional peaks at 16.7, 19.6, 22.4, 25.1 and 25.9 degrees two theta±0.2 degrees two theta. Preferably, crystalline form VI of prasugrel hydrobromide can be a THF solvate.

The present invention provides a crystalline form of Prasugrel hydrobromide, designated as Form VII. Form VII can be characterized by data selected from: an X-ray powder diffraction pattern having peaks at 8.1, 8.4, 11.9, 20.6 and 23.6 degrees two theta±0.2 degrees two theta; an XRPD pattern substantially as depicted in FIG. 10; a solid-state $^{13}C$ NMR spectrum having peaks at 20.8, 30.4, 36.4, 110.2 and 125.9±0.2 ppm; a solid-state $^{13}C$ NMR spectrum substantially as depicted in FIG. 25 and combinations thereof, Form VII can be further characterized by a powder XRD pattern having additional peaks at 12.7, 13.0, 15.4, 22.8 and 26.2 degrees two theta±0.2 degrees two theta. Preferably, crystalline form VII of prasugrel hydrobromide can be a methyl ethyl ketone ("MEK") solvate.

The present invention provides a crystalline form of Prasugrel hydrobromide, designated as Form IA. Form IA can be characterized by data selected from: an X-ray powder diffraction pattern having peaks at 7.9, 8.1, 13.5, 14.6 and 25.2 degrees two theta±0.2 degrees two theta; an XRPD pattern substantially as depicted in FIG. 11; and combinations thereof. Form IA can be further characterized by a powder XRD pattern having additional peaks at 16.8, 21.4, 23.7, 24.9 and 27.2 degrees two theta±0.2 degrees two theta. Preferably, crystalline Form IA of prasugrel hydrobromide can be anhydrous.

The present invention provides a crystalline form of Prasugrel hydrobromide, designated as Form VIII. Form VIII can be characterized by data selected from: an X-ray powder diffraction pattern having peaks at 11.9, 12.7, 12.9, 15.3 and 24.7 degrees two theta±0.2 degrees two theta; an XRPD pattern substantially as depicted in FIG. 12; and combinations thereof. Form VIII can be further characterized by a powder XRD pattern having additional peaks at 8.5, 20.6, 23.4, 26.1 and 27.2 degrees two theta±0.2 degrees two theta. Preferably, crystalline form VIII of prasugrel hydrobromide can be a 1-butanol solvate.

The present invention provides a crystalline form of Prasugrel hydrobromide, designated as Form IX. Form IX can be characterized by data selected from: an X-ray powder diffraction pattern having peaks at 8.5, 13.0, 15.4, 20.8 and 24.7 degrees two theta±0.2 degrees two theta; an XRPD pattern substantially as depicted in FIG. 13; and combinations thereof. Form IX can be further characterized by a powder XRD pattern having additional peaks at 8.0, 11.9, 12.8, 18.3 and 22.9 degrees two theta±0.2 degrees two theta.

The present invention provides a crystalline form of Prasugrel hydrobromide, designated as Form X. Form X can be characterized by data selected from: an X-ray powder diffraction pattern having peaks at 10.3, 12.4, 14.0, 18.0 and 18.7 degrees two theta±0.2 degrees two theta; an XRPD pattern substantially as depicted in FIG. 14; and combinations thereof. Form X can be further characterized by a powder XRD pattern having additional peaks at 7.2, 14.5, 22.1, 24.8 and 26.3 degrees two theta±0.2 degrees two theta.

The present invention provides a crystalline form of Prasugrel hydrobromide, designated as Form XI. Form XI can be characterized by data selected from: an X-ray powder diffraction pattern having peaks at 8.6, 12.5, 14.5, 22.2 and 24.8 degrees two theta±0.2 degrees two theta; an XRPD pattern substantially as depicted in FIG. 15; and combinations thereof. Form XI can be further characterized by a powder XRD pattern having additional peaks at 7.3, 7.9, 14.1, 18.1 and 18.7 degrees two theta±0.2 degrees two theta.

The present invention provides a crystalline form of Prasugrel hydrobromide, designated as form XII. Form XII can be characterized by data selected from: an X-ray powder diffraction pattern having peaks at 8.3, 12.6, 12.9, 20.4 and 23.5 degrees two theta±0.2 degrees two theta; an XRPD pattern substantially as depicted in FIG. 16; and combinations thereof. Form XII can be further characterized by a powder XRD pattern having additional peaks at 8.1, 13.0, 18.3, 19.4 and 24.3 degrees two theta±0.2 degrees two theta.

The present invention provides a crystalline form of Prasugrel hydrobromide, designated as form XIII. Form XIII can be characterized by data selected from: an X-ray powder diffraction pattern, having peaks at 8.0, 8.3, 11.9, 15.2 and 20.2 degrees two theta±0.2 degrees two theta; an XRPD pattern substantially as depicted in FIG. 17; and combinations thereof. Form XIII can be further characterized by a powder XRD pattern having additional peaks at 12.4, 13.0, 17.5, 18.3 and 23.4 degrees two theta±0.2 degrees two theta. Typically, crystalline form XIII of prasugrel hydrobromide can be an n-butyl acetate solvate.

The present invention further provides a crystalline form of Prasugrel phosphate, designated as Form P1. Form P1 can be characterized by data selected from: an X-ray powder diffraction pattern having peaks at 6.7, 8.0, 15.0, 20.3 and 26.5 degrees two theta±0.2 degrees two theta; an XRPD pattern substantially as depicted in FIG. 18; and combinations thereof. Form P1 can be further characterized by a powder XRD pattern having additional peaks at 10.1, 10.6, 14.2, 22.3 and 25.9 degrees two theta±0.2 degrees two theta.

The present invention further provides a crystalline form of Prasugrel phosphate, designated as Form P2. Form P2 can be characterized by data selected from: an X-ray powder diffraction pattern having peaks at 6.6, 8.1, 16.2, 20.0 and 22.9 degrees two theta±0.2 degrees two theta; an XRPD pattern substantially as depicted in FIG. 19; and combinations thereof. Form P2 can be further characterized by a powder XRD pattern having additional peaks at 12.3, 13.2, 17.0, 18.3 and 24.8 degrees two theta±0.2 degrees two theta.

The present invention also provides a crystalline form of Prasugrel hydrogen sulfate, designated as Form S1. Form S1 can be characterized by data selected from: an X-ray powder diffraction pattern having peaks at 8.8, 9.3, 12.9, 22.9 and 23.2 degrees two theta±0.2 degrees two theta; an XRPD pattern substantially as depicted in FIG. 20; and combinations thereof. Form S1 can be further characterized by a powder XRD pattern having additional peaks at 10.1, 14.0, 21.7, 22.6 and 24.4 degrees two theta 0.2 degrees two theta.

The present invention also provides a crystalline form of Prasugrel hydrogen sulfate, designated as form S2. Form S2 can be characterized by data selected from: an X-ray powder diffraction pattern having peaks at 8.2, 9.5, 9.9, 18.3 and 24.5 degrees two theta±0.2 degrees two theta; an XRPD pattern substantially as depicted in FIG. 21; and combinations thereof. Form S2 can be further characterized by a powder XRD pattern having additional peaks at 12.2, 14.6, 16.2, 19.8 and 25.1 degrees two theta±0.2 degrees two theta.

The present invention provides a crystalline form of Prasugrel hydrogen sulfate, designated as form S3. Form S3 can be characterized by data selected from: an X-ray powder diffraction pattern having peaks at 14.5, 19.3, 21.1, 22.5 and 24.1 degrees two theta±0.2 degrees two theta; an XRPD pattern substantially as depicted in FIG. 22; and combinations thereof. Form S3 can be further characterized by a powder XRD pattern having additional peaks at 9.5, 9.8, 12.2, 17.7 and 24.8 degrees two theta±0.2 degrees two theta.

The above salts and solid state forms of Prasugrel can be used to prepare Prasugrel hydrochloride and formulations thereof, preferably for reducing the aggregation ("clumping") of platelets. The above described salts and crystalline forms can be converted to Prasugrel hydrochloride by a process comprising reacting Prasugrel salt with a base to obtain Prasugrel base and further reacting with hydrochloric acid to obtain Prasugrel hydrochloride. The process can be done for example according U.S. Pat. No. 6,693,115 B2 examples 1, 3, 4 and 6.

The present invention further encompasses 1) a pharmaceutical composition comprising the above described salts and crystalline forms and at least one pharmaceutically acceptable excipient; 2) the use of any one or combination of the above described salts and crystalline forms in the manufacture of a pharmaceutical composition, 3) the use of any one of the above pharmaceutical compositions for reducing the aggregation ("clumping") of platelets and 4) a method of inhibiting aggregation ("clumping") of platelets, comprising administering a pharmaceutically effective amount of at least one of the above described salts and crystalline forms to a subject in need of the treatment. The pharmaceutical composition can be useful for preparing a medicament. The present invention also provides at least one of the above described salts and crystalline forms for use as a medicament.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Instrumentation

X-Ray Powder Diffraction:

X-ray powder diffraction (XRPD) was performed on Philips X'Pert PRO powder diffractometer equipped with X'Celerator detector (active length 2Θ2.022°, CuKα radiation, λ=1.54184 Å at laboratory temperature 22-25° C. Prior to analysis the samples were gently ground by means of mortar and pestle in order to obtain a fine powder and applied directly on silicon zero background holder. The scanning parameters were: range: 3-40 degrees two-theta: scan mode: continuous scan; step size: 0.0167°; and time per step: 37 sec.

The described peak positions were determined by using a silicon powder as an internal standard in an admixture with the sample measured. The position of the silicon (Si) peak was corrected to silicone theoretical peak: 28.45 degrees two theta, and the positions of the measured peaks were corrected respectively.

Solid-state $^{13}$C NMR:

Solid-state $^{13}$C NMR spectra were recorded with variable amplitude cross polarization, magic angle spinning and high power proton decoupling using a BRUKER Avance II+ spectrometer operating at 125 MHz and ambient temperature (about 25° C.—not controlled). A probe using 4 mm o.d. zirconia rotors was employed. The operation conditions were: contact time:2 ms; recycle delay: 25s 256 scans for form I; recycle delay 5s 1024 scans for forms III and VII; spin rate of 11 kHz. Chemical shifts were referenced via a replacement sample of glycine (carboxyl carbon chemical shift assigned as 176.03 ppm relative to the signal of tetramethylsilane).

EXAMPLES

Reference Examples

Prasugrel hydrochloride forms A and B and prasugrel base may be prepared according to U.S. Pat. No. 6,693,115, Examples 1, 3 and Reference example 1 (respectively), incorporated herein by reference.

Example 1

Preparation of Prasugrel Hydrochloride Nitromethane Solvate

Prasugrel hydrochloride (30 mg) was dissolved in 0.5 ml of nitromethane by heating to 60° C. in a bottle. The bottle was sealed and left at 25° C. to crystallize. After three days, white crystals were obtained. The XRPD pattern of the crystals is shown in FIG. 1.

Example 2

Preparation of Crystalline Prasugrel Hydrochloride Form F, Acetic Acid Solvate

Prasugrel hydrochloride (35 mg) was dissolved in 0.5 ml acetic anhydride at 24° C. The atmosphere above the solution was kept inert with nitrogen, and the bottle was sealed and left at 24° C. under nitrogen to crystallize. After 5 days white crystals were obtained.

Example 3

Preparation of Crystalline Prasugrel Hydrochloride Form F, Acetic Acid Solvate

Prasugrel base (10 mg) was dissolved in 150 µl tert-butyl acetate at 24° C. in a test tube. Glacial acetic acid (0.025 ml) and chlorotrimethylsilane (0.025 ml) were added to the solution. Immediately after addition of chlorotrimethylsilane, a white precipitate was obtained. After shaking the test tube, the precipitate turned to oil drops. The test tube was sealed and left at 24° C. to crystallize. After two days white crystals were obtained.

Example 4

Preparation of Crystalline Prasugrel Hydrochloride Form F, Acetic Acid Solvate

Prasugrel base (10 mg) was dissolved in 150 µl isopropyl acetate by heating to about 60° C. in a test tube. Glacial acetic acid (0.025 ml) and chlorotrimethylsilane (0.025) were added to the solution at 24° C. Immediately after addition of chlorotrimethylsilane, a white precipitate was obtained. After shaking the test tube, the precipitate turned to oil drops. The test tube was sealed and left at 24° C. to crystallize. After two days white crystals were obtained.

Example 5

Preparation of Crystalline Prasugrel Hydrochloride Form F, Acetic Acid Solvate

Prasugrel base (10 mg) was dissolved in 150 µl methyl-tert-buthyl ether by heating to about 40° C. in a test tube. Glacial acetic acid (0.025 ml) and chlorotrimethylsilane (0.025 ml) were added to the solution at 24° C. Immediately after addition of chlorotrimethylsilane a white precipitate was obtained. After shaking the test tube, the precipitate turned to oil drops. The test tube was sealed and left at 24° C. to crystallize. After two days white crystals were obtained.

Example 6

Preparation of Crystalline Prasugrel Hydrochloride Form F, Acetic Acid Solvate

Prasugrel base (10 mg) was dissolved in 150 µl tetrachloromethane by heating to about 50° C. in a test tube. Glacial acetic acid (0.025 ml) and chlorotrimethylsilane (0.025 ml) were added to the solution at 24° C. immediately after addition of chlorotrimethylsilane a white precipitate was obtained. After shaking the test tube, the precipitate turned to oil drops. The test tube was sealed and left at 24° C. to crystallize. After two days white crystals were obtained.

Example 7

Preparation of Crystalline Prasugrel Hydrochloride Form F, Acetic Acid Solvate

Prasugrel base (10 mg) was suspended in 150 µl p-cymol by heating to about 70° C. in a test tube. The clear solution was decanted. Glacial acetic acid (0.025 ml) and chlorotrimethylsilane (0.025 ml) were added to the solution at 24° C. Immediately after addition of chlorotrimethylsilane a white precipitate was obtained. After shaking the test tube, the precipitate turned to oil drops. The test tube was sealed and left at 24° C. to crystallize. After two days white crystals were obtained.

Example 8

Preparation of Crystalline Prasugrel Hydrochloride Form F, Acetic Acid Solvate

Prasugrel base (10 mg) was dissolved in 150 µl ethyl acetate by heating to about 60° C. in a test tube. Glacial acetic acid (0.025 ml) and chlorotrimethylsilane (0.025 ml) were added to the solution at 24° C. Immediately after addition of chlorotrimethylsilane, a white precipitate was obtained. After shaking the test tube, the precipitate turned to oil drops. The test tube was sealed and left at 24° C. to crystallize. After two days white crystals were obtained.

Example 9

Preparation of Crystalline Prasugrel Hydrochloride Form F, Acetic Acid Solvate

Prasugrel base (10 mg) was dissolved in 150 µl mesitylene by heating to about 60° C. in a test tube. Glacial acetic acid (0.025 ml) and chlorotrimethylsilane (0.025 ml) were added to the solution at 24° C. Immediately after addition of chlorotrimethylsilane a white precipitate was obtained. After shaking the test tube, the precipitate turned to oil drops. The test tube was sealed and left at 24° C. to crystallize. After two days white crystals were obtained.

Example 10

Preparation of Crystalline Prasugrel Hydrochloride Form F, Acetic Acid Solvate

Prasugrel base (10 mg) was dissolved in 150 µl isobutyl acetate by heating to about 60° C. in a test tube. Glacial acetic acid (0.025 ml) and chlorotrimethylsilane (0.025 ml) were added to the solution at 24° C. Immediately after addition of chlorotrimethylsilane a white precipitate was obtained. After shaking the test tube, the precipitate turned to oil drops. The test tube was sealed and left at 24° C. to crystallize. After two days white crystals were obtained.

Example 11

Preparation of Crystalline Prasugrel Hydrochloride Form F, Acetic Acid Solvate

Prasugrel hydrochloride form B (199 mg) was dissolved in 9 ml of acetic anhydride at 70° C. The solution was cooled down to room temperature (20-25° C.) and stirred for 6 hours. Next, the solution was seeded with a few crystals of prasugrel hydrochloride form F and left over night to stir at room temperature (20-25° C.). The weak suspension was stirred for 24 hours at 0-5° C. The crystals that formed were collected by filtration. The crystals were dried over night at room temperature. Off-white crystals of prasugrel hydrochloride form F were obtained. Yield: 45.2%.

Example 12

Preparation of Crystalline Prasugrel Hydrochloride Form F, Acetic Acid Solvate

Prasugrel hydrochloride form B (200 mg) was dissolved in 1 ml glacial acetic acid at 50° C. The solution was then cooled down to room temperature (20-25° C.) and left for 4 hours to crystallize. The resulting suspension was filtered and the filtered crystals were washed with 0.3 ml glacial acetic acid. The crystals were dried overnight at room temperature (20-25° C.). Off-white crystals of prasugrel hydrochloride form F were obtained. Yield: 63.5%.

Example 13

Preparation of Crystalline Prasugrel Hydrochloride Form F, Acetic Acid Solvate

Prasugrel hydrochloride form B (1.0 g) was dissolved in 4 ml of glacial acetic acid at 40° C., cooled down to room temperature (20-25° C.) and left for 3 hours to crystallize. The resulting suspension was filtered and the crystals were washed with 2.0 ml glacial acetic acid. The crystals were dried overnight at room temperature (20-25° C.). Off-white crystals of prasugrel hydrochloride form F were obtained. Yield: 90.8%.

Example 14

Preparation of Crystalline Prasugrel Hydrochloride Form F, Acetic Acid Solvate

Prasugrel hydrochloride form B (499 mg) was suspended in 3 ml glacial acetic acid at room temperature (20-25° C.). The weak suspension was stirred at room temperature for 3 hours to crystallize and was then filtered. The filtered crystals were washed with 1 ml glacial acetic acid. Off-white crystals of prasugrel hydrochloride form F were obtained. Yield: 83.8%.

Example 15

Preparation of Crystalline Prasugrel Hydrochloride Form F, Acetic Acid Solvate

Prasugrel hydrochloride form B (499 mg) was suspended in 3 ml glacial acetic acid at room temperature (20-25° C.). The resulting weak suspension was stirred at room temperature for 3 hours to crystallize and was then filtered. The filtered crystals were washed with 1 ml glacial acetic acid and dried overnight at room temperature (20-25° C.). Off-white crystals of prasugrel hydrochloride form F were obtained. Yield: 80.9%.

Example 16

Preparation of Crystalline Prasugrel Hydrochloride Form F, Acetic Acid Solvate

Prasugrel hydrochloride form B (1.001 g) was dissolved in 4 ml glacial acetic acid at 40° C., cooled down to room temperature (20-25° C.) and left to crystallize for 3 hours. The filtered crystals were washed with 2 ml glacial acetic acid and 1 ml distilled water. The crystals were dried overnight at room temperature (20-25° C.). Yellowish crystals of prasugrel hydrochloride form F were obtained. Yield: 62.9%.

Example 17

Preparation of Crystalline Prasugrel Hydrochloride Acetic Acid Solvate

Prasugrel hydrochloride form B (15.005 g) was dissolved in 60 ml glacial acetic acid at 40° C., then cooled down to room temperature (20-25° C.) and left to crystallize for 4.5 hours. The resulting crystals were filtered and washed with 20 ml glacial acetic acid (5+15 ml in portions), dried for 30 min at 30° C./10 mbar, and left overnight at room temperature (20-25° C.). Off-white crystals of prasugrel hydrochloride form F were obtained.
Yield: 87.9%.

Example 18

Preparation of Crystalline Prasugrel Hydrochloride Form F, Acetic Acid Solvate

Prasugrel hydrochloride form A (1.295 g) was dissolved in 6.5 ml glacial acetic acid at 60° C., cooled down to room temperature (20-25° C.) and left to crystallize for 5 hours. The resulting crystals were filtered and washed with 3 ml glacial acetic acid (2+1 ml in portions) and dried for 30 min at 30° C./10 mbar, and left overnight at room temperature (20-25° C.). Off-white crystals of prasugrel hydrochloride form F were obtained. Yield: 70.3%.

Example 19

Preparation of Crystalline Form of Prasugrel Nitrate

To a solution of 251 mg of prasugrel base form I in 3.75 ml acetone at room temperature (20-25° C.), a solution of 50.6 μl (1.1 eq) 65% aqueous nitric acid in 1.25 ml acetone was added in portions and the resulting mixture was stirred at room temperature for about 15 minutes. After addition of 5 ml heptane at 0-5° C. (ice bath), the clear reaction mixture turned to an emulsion (clear oil drops on the bottom of the flask). A white precipitate was obtained after storage for 17 hours at about −25° C. The mixture containing the precipitate was stirred for 1 hour at 0-5° C. (ice bath), filtered off, washed with 1 ml cold acetone/heptane (1:1) and dried at 40° C./10 mbar for about 2.5 hours. White crystals (269 mg) of prasugrel nitrate were obtained.

Example 20

Preparation of Crystalline Form of Prasugrel Nitrate

To a solution of 504 mg of prasugrel base form I in 5 ml acetone at room temperature (20-25° C.), a solution of 101.2 µl (1.1 eq) 65% aqueous nitric acid in 2 ml acetone was added. After 10 minutes, the resulting clear reaction mixture was seeded with a small amount of prasugrel nitrate (prepared according to example 11) and the resulting mixture was stirred for 4 hours at 0-5° C. (ice bath) to crystallize. A white precipitate formed and was filtered off, washed with 1 ml acetone and dried at 40° C./10 mbar for 17 hours. White crystals (350 mg) of prasugrel nitrate were obtained.

Example 21

Preparation of Crystalline Form II of Prasugrel Hydrobromide

Prasugrel base (1.00 g) was dissolved in acetone (15.5 ml) at 20-25° C. Solution of 0.34 ml 47% HBr in 4.8 ml of acetone was added in solution of base. Clear solution was cooled down to 5-0° C. After 5 minutes crystallization took place. Suspension was stirred at 5-0° C. for 2 hours, filtered, crystals were washed with acetone and dried at 40° C./vacuum, yielding form II of prasugrel hydrobromide (1.26 g). HPLC purity: 99.94%.

The sample was left in an open Petri dish at room conditions (20-25° C., relative humidity 20-30%) for 1 month and then reanalyzed on HPLC giving purity of 99.84%.

Example 22

Preparation of Crystalline Form II of Prasugrel Hydrobromide

Prasugrel base (2.00 g) was dissolved in acetone (20 ml) at 20-25° C. A solution of 0.41 ml 47% HBr in 8 ml of acetone was added over 10 minutes. Crystallization took place immediately. The resulting suspension was stirred at 20-25° C. for 1.5 hours and than 2 hours at 5-0° C. Crystals formed and were filtered, washed with acetone and dried at 40° C./vacuum, yielding form II of prasugrel hydrobromide (1.75 g). HPLC purity: 99.67%.

Example 23

Preparation of Crystalline Form II of Prasugrel Hydrobromide

A solution of prasugrel base (1.506 g) in acetone (30 ml) at 20-25° C. under nitrogen atmosphere, was sparged with hydrogen bromide gas until pH≈0.5 with stirring. Crystallization occurred after about 5 minutes. After 30 minutes, the resulting suspension was cooled down to 5-0° C. and stirred for 2 hours. Crystals were filtered off under a nitrogen atmosphere, washed with 6 ml of acetone ((4+2) ml in portions) and dried at 30° C./10 mbar for about 45 minutes. Form II of Prasugrel hydrobromide (1.941 g) was obtained.

Example 24

Preparation of Crystalline Form II of Prasugrel Hydrobromide

To a solution of prasugrel base (0.998 g) in acetone (16 ml) at 20-25° C. under nitrogen atmosphere was added dropwise a solution of 0.34 ml 47% HBr(aq) in 4 ml of acetone. Crystallization occurred during the addition. After 30 minutes, the resulting suspension was cooled down to 5-0° C. and stirred for 2 hours. Crystals were filtered off under a nitrogen atmosphere, washed with 6 ml of acetone ((4+2) ml in portions) and dried at 30° C./10 mbar for about 45 minutes. Form II of Prasugrel hydrobromide (1.269 g) was obtained.

Example 25

Preparation of Crystalline Form III of Prasugrel Hydrobromide

Prasugrel base (1.00 g) was suspended in 2-propanol (10.0 ml) at 40° C. A solution of 0.34 ml 47% HBr in 5.0 ml of 2-propanole was added. The resulting clear solution was cooled down to 20-25° C. and seeded with prasugrel hydrobromide crystals. Crystallization took place immediately. The resulting suspension was stirred at 20-25° C. for 1.5 hours. The crystals that formed were filtered, washed with 2-propanol and dried at 40° C./vacuum, yielding Form III of prasugrel hydrobromide (1.25 g). HPLC purity: 99.39%.

Example 26

Preparation of Crystalline Form I of Prasugrel Hydrobromide

About 30 mg of prasugrel hydrobromide form II was suspended in 5 ml of ethyl acetate by heating to about 60° C. and the suspension was then filtered. The resulting filtrate was left at 20-25° C. to crystallize by cooling and evaporation. After 4 days, the crystals that formed were filtered off and dried at 60° C./10 mbar for about 3 hours. Crystals of form I of prasugrel hydrobromide were obtained.

Example 27

Preparation of Crystalline Form I of Prasugrel Hydrobromide

About 30 mg of prasugrel hydrobromide form II was dissolved in 3 ml of methyl ethyl ketone by heating to about 50° C. The resulting solution was left at 20-25° C. to crystallize by cooling and evaporation. After 4 days, the crystals that formed were filtered off and dried at 60° C./10 mbar for about 3 hours. Crystals of form I of prasugrel hydrobromide were obtained.

Example 28

Preparation of Crystalline Form I of Prasugrel Hydrobromide

To a suspension of 0.500 g of prasugrel base in 7.31 ml of methyl iso-butyl ketone/4.2% methanol at 20-25° C., was added dropwise a solution of 0.17 ml 47% HBr(aq) in 3 ml of methyl iso-butyl ketone. The resulting clear reaction mixture was seeded with small amount of crystalline Form I of prasugrel hydrobromide. Crystallization occurred immediately. After 30 minutes the resulting suspension was cooled down to 0-5° C. and stirred for about 2 hours. The crystals were filtered off, washed with 0.5 ml methyl iso-butyl ketone and dried at 40° C./10 mbar for about 3 hours. Prasugrel hydrobromide (0.524 g) was obtained.

Example 29

Preparation of Crystalline Form I of Prasugrel Hydrobromide

To a suspension of 0.499 g of prasugrel base in 5.29 ml of isopropyl acetate/5.5% methanol at 20-25° C., was added dropwise a solution of 0.17 ml 47% HBr(aq) in 1.53 ml of isopropyl acetate/2% methanol. Crystallization occurred to form fluffy crystals. After 45 minutes the resulting suspension was cooled down to 0-5° C. and stirred for about 4 hours. The crystals were filtered off, washed with 1 ml of isopropyl acetate and dried at 40° C./10 mbar for about 17 hours, Prasugrel hydrobromide (0.553 g) was obtained.

Example 30

Preparation of Crystalline Form IV of Prasugrel Hydrobromide

About 30 mg of prasugrel hydrobromide form II was dissolved in 1 ml of 96% ethanol at 20-25° C. The resulting solution was left at 20-25° C. to crystallize by evaporation. After 4 days, the resulting crystals were filtered off and dried at 60° C./10 mbar for about 3 hours. Crystals of form IV of prasugrel hydrobromide were obtained.

Example 31

Preparation of Crystalline Form V of Prasugrel Hydrobromide

About 30 mg of prasugrel hydrobromide form II was dissolved in acetic acid (1 ml) by heating to about 50° C. The resulting solution was left at 20-25° C. to crystallize by cooling and evaporation. After 4 days the crystals were filtered off and dried at 60° C./10 mbar for about 3 hours. Crystals of form V of prasugrel hydrobromide were obtained.

Example 32

Preparation of Crystalline Form VI of Prasugrel Hydrobromide

About 30 mg of prasugrel hydrobromide form H was suspended in 5 ml of tetrahydrofuran ("THF") by heating to about 55° C. and the suspension was then filtered. The clear filtrate was left at 20-25° C. to crystallize by cooling and evaporation. After 4 days, the crystals formed therein were filtered off and dried at 60° C./10 mbar for about 3 hours. Crystals of form VI of prasugrel hydrobromide were obtained.

Example 33

Preparation of Crystalline Form VII of Prasugrel Hydrobromide

To a solution of 0.503 g of prasugrel base in 5 ml of methyl ethyl ketone at 20-25° C., was added dropwise a solution of 0.17 ml of 47% HBr (aq) in 2 ml of methyl ethyl ketone. Crystallization occurred at the end of the addition. After 2 hours, the resulting suspension was cooled down to 0-5° C. and stirred for about 30 minutes. The crystals that had formed were filtered off, washed with 1 ml of methyl ethyl ketone and dried at 40° C./10 mbar for about 3 hours. Prasugrel hydrobromide (0.595 g) was obtained.

Example 34

Preparation of Crystalline Form VII of Prasugrel Hydrobromide

Prasugrel base (5.00 g) was dissolved in 50.0 ml of methyl ethyl ketone. A solution of 1.7 ml of 47% HBr (aq) in 20 ml of methyl ethyl ketone was added. Prasugrel hydrobromide crystallized after 5 minutes. The resulting suspension was stirred at room temperature for 1 hour and then 0.5 hours at 0-5° C. The crystals that formed were filtered, washed with methyl ethyl ketone and dried at 50° C./vacuum, yielding 6.06 g of prasugrel hydrobromide.

Example 35

Preparation of Crystalline Form IA of Prasugrel Hydrobromide

To a suspension of 0.403 g of prasugrel base in 5 ml of isopentanol at 20-25° C., was added dropwise a solution of 0.136 ml of 47% HBr (aq) in 1 ml of isopentanol. After 1 hour the resulting clear reaction mixture was cooled down to 0-5° C., seeded with a small amount of crystalline form I of prasugrel hydrobromide, stirred for about 3 hours at 0-5° C. and then stirred for about 17 hours at 8-10° C. The crystals that formed were filtered off and dried at 40° C./10 mbar for about 3 hours. Prasugrel hydrobromide (0.321 g) was obtained.

Example 36

Preparation of Crystalline Form IA of Prasugrel Hydrobromide

To a suspension of 0.500 g of prasugrel base in 5 ml of 1-pentanol at 20-25° C., was added dropwise a solution of 0.17 ml of 47% HBr(aq) in 1 ml of 1-pentanol. After 30 minutes, the resulting clear reaction mixture was cooled down to 0-5° C., seeded with a small amount of prasugrel hydrobromide crystalline form 1A, and stirred for about 5 hours at 0-5° C. and for about 17 hours at 8-10° C. Crystals formed and were filtered off, washed with 2 ml of 1-pentanol and dried at 40° C./10 mbar for about 5 hours. Prasugrel hydrobromide (0.342 g) was obtained.

Example 37

Preparation of Crystalline Form IA of Prasugrel Hydrobromide

To a suspension of 0.503 g of prasugrel base in 3.3 ml of methyl acetate/9.1% methanol at 20-25° C., was added dropwise a solution of 0.17 ml of 47% HBr(aq) in 1 ml of methyl acetate. The resulting clear reaction mixture was seeded with a small amount of prasugrel hydrobromide crystalline Form I. Crystallization occurred immediately. After 45 minutes, the suspension was cooled down 0-5° C. and stirred for about 3 hours. Crystals formed and were filtered off, washed with 3 ml of methyl acetate (2×1.5 ml in portions) and dried at 40° C./10 mbar for about 17 hours. Prasugrel hydrobromide (0.496 g) was obtained.

Example 38

Preparation of Crystalline Form IA of Prasugrel Hydrobromide

To a solution of 0.504 g of prasugrel base in 5.12 ml of methyl acetate/2.4% methanol at 20-25° C., was added dropwise a solution of 0.17 ml of 47% HBr(aq) in 1 ml of methyl acetate. The resulting clear reaction mixture was seeded with a small amount of prasugrel hydrobromide crystalline Form I. Crystallization occurred immediately. After 45 minutes the suspension was cooled down to 0-5° C. and stirred for about 3 hours. Crystals formed and were filtered off, washed with 3 ml of methyl acetate (2×1.5 ml in portions) and dried at 40° C./10 mbar for about 17 hours. Prasugrel hydrobromide (0.529 g) was obtained.

Example 39

Preparation of Crystalline Form VIII of Prasugrel Hydrobromide

Prasugrel base (0.51 g) was suspended in 5.0 ml of 1-butanol. A solution of 0.17 ml of 47% HBr (aq) in 2.5 ml of 1-butanol was added to form a clear solution. After 15 minutes at room temperature crystallization started. The resulting suspension was cooled to 0-5° C. and stirred for 1.5 hour. Crystals formed and were filtered, washed with 1-butanol and dried at 50° C./vacuum, yielding 0.53 g of prasugrel hydrobromide.

Example 40

Preparation of Crystalline Form IX of Prasugrel Hydrobromide

A solution of prasugrel base (2.454 g) in 30 ml of methyl acetate/2% methanol at 20-25° C. was seeded with small amount of prasugrel hydrobromide form I. The resulting suspension was purged with hydrogen bromide gas until a pH of 2.0-2.5 was obtained. The reaction mixture was seeded again with small amount of prasugrel hydrobromide form I at about pH of 3.6. The suspension was then stirred for about 45 minutes at 20-25° C. and then cooled to 5-0° C. for about 4 hours. Crystals formed and were filtered under an inert atmosphere, washed with 2 ml of methyl acetate and dried at 40° C./10 mbar for about 17 hours. Prasugrel hydrobromide (2.805 g) was obtained.

Example 41

Preparation of Crystalline Form X of Prasugrel Hydrobromide

To a solution of prasugrel base (0.500 g) in 7.29 ml of toluene/4% methanol at 20-25° C., hydrogen bromide gas was purged until a pH of 2.0-2.5 was obtained. During the purging, the clear reaction mixture was seeded with small amount of prasugrel hydrobromide form I. The resulting suspension was stirred at 20-25° C. for about 45 minutes and then cooled to 0-5° C. for about 3 hours. Crystals formed and were filtered, washed with 1 ml of toluene and dried at 40° C./10 mbar for about 17 hours. Prasugrel hydrobromide Form X (0.149 g) was obtained.

Example 41

Preparation of Crystalline Form XI of Prasugrel Hydrobromide

To a suspension of prasugrel base (2.357 g) in 30 ml of isobutyl acetate/5.5% MeOH at 20-25° C., hydrogen bromide was purged until a pH of 2.0-2.5 was obtained. After the purging, the suspension was stirred at 20-25° C. for about 45 minutes and then cooled to 0-5° C. for about 3.5 hours. Crystals were formed, filtered under an inert atmosphere, washed with (2+2) ml of isobutyl-acetate and dried at 40° C./10 mbar for about 18 hours. Prasugrel hydrobromide form XI was obtained (2.275 g).

Example 42

Preparation of Crystalline Form XII of Prasugrel Hydrobromide

To a solution of prasugrel base (2.453 g) in 30 ml of methyl acetate/2% MeOH at 20-25° C., hydrogen bromide was purged until pH of 2.2-2.7 was obtained (by pH-meter). After the purging, the suspension was stirred at 20-25° C. for about 45 minutes and cooled to 0-5° C. for about 2 hours. Crystals were obtained, filtered under an inert atmosphere, washed with (2+2) ml of methyl acetate and dried at 40° C./10 mbar for about 18 hours. Prasugrel hydrobromide form XII was obtained (1.039 g).

Example 43

Preparation of Crystalline Form XII of Prasugrel Hydrobromide

To the mother liquor obtained according to example 42, hydrogen bromide was purged again until a pH of 2.5-3 was obtained (by indicator paper). A suspension was obtained and stirred at 20-25° C. for about 20 minutes and then cooled to 0-5° C. for about 45 minutes. The obtained crystals were filtered under an inert atmosphere, washed with (2+2) ml of methyl acetate and dried at 40° C./0 mbar for about 15.5 hours. Prasugrel hydrobromide form XII was obtained (1.727 g).

Example 44

Preparation of Crystalline Form XIII of Prasugrel Hydrobromide

To a suspension of prasugrel base (0.501 g) in 6.0 ml of n-butyl acetate at 20-25° C., a dropwise solution of 0.170 ml of 47% HBr(aq) in 1.0 ml of n-butyl acetate was added. After the first drop of the acid solution, 0.3 ml of methanol was added. After the addition, the suspension was stirred at 20-25° C. for about 30 minutes and cooled to 0-5° C. for about 2 hours. The obtained crystals were filtered, washed with 1 ml of n-butyl acetate and dried at 40° C./10 mbar for about 22 hours. Prasugrel hydrobromide form XIII was obtained (0.616).

Example 45

Preparation of Crystalline Form P1 of Prasugrel Phosphate

To a solution of prasugrel base (1.006 g) in 21.67 ml of methyl acetate/7.7% ethanol at 20-25° C., a dropwise solution of 99% phosphoric acid (329.9 mg) in 2 ml of methyl acetate was added. Crystallization occurred within 30 minutes. After 3 hours at 20-25° C., the suspension was cooled to 0-5° C. and stirred for about 2 hours at that temperature. The obtained crystals were filtered, washed with 4 ml of methyl acetate and dried at 40° C./vacuum for about 1.5 hours. Prasugrel phosphate Form P1 (0.883 g) was obtained.

Example 46

Preparation of Crystalline Form P2 of Prasugrel Phosphate

To a solution of prasugrel base (0.252 g of) in 2.0 ml of dichloromethane at 0-5° C., a dropwise solution of 55.0 µL of 85% $H_3PO_4$ (aq) was added. An oily reaction mixture was obtained and stirred at 0-5° C. for about 7 hours and for an additional 17 hours at 8-10° C. The obtained crystals were filtered and dried at 40° C./vacuum for about 5 hours. Prasugrel phosphate form P2 was obtained (0.186 g).

Example 47

Preparation of Crystalline Form S1 of Prasugrel Hydrogen Sulfate

To a solution of prasugrel base (0.399 g) in 6.19 ml of methyl acetate/3% methanol at 0-5° C., a dropwise solution of 58.6 µl of conc, sulfuric acid was added. After about 4 hours at 0-5° C. the clear reaction mixture was stored at −20° C. for about 17 hours without stirring, then warmed again to 0-5° C. and seeded with a small amount of prasugrel hydrogen sulfate Form S1. The resulting suspension was left for 2 days at −20° C. The thus-obtained crystals were mixed again at 0-5° C. for about 30 minutes, filtered, washed with 1 ml of methyl acetate and dried at 40° C./vacuum for about 3 hours. Prasugrel hydrogen sulfate Form S1 (63 mg) was obtained.

Example 48

Preparation of Crystalline Form S1 of Prasugrel Hydrogen Sulfate

To a solution of prasugrel base (0.204 g) in 2.34 ml of methyl acetate/1.5% ethanol at 0-5° C., a dropwise solution of 29.3 µl of conc. sulfuric acid was added. The resulting oily reaction mixture was warmed to 20-25° C. for about 30 minutes, then cooled again to 0-5° C., seeded with small amount of prasugrel hydrogen sulfate Form S1 and stirred for about 3 hours. The thus-obtained crystals were filtered and dried at 40° C./vacuum for about 17 hours. Prasugrel hydrogen sulfate (63 mg) was obtained. The flask was washed with 2 ml of methyl acetate, left crystals were filtered separately, and dried at 40° C./vacuum for about 17 hours. Prasugrel hydrogen sulfate (84 mg) was obtained.

Example 49

Preparation of Crystalline Form S1 of Prasugrel Hydrogen Sulfate

To a solution of 0.156 ml of conc. sulfuric acid in 3.13 ml of acetone at −25° C., a dropwise solution of prasugrel base (0.500 g) in 4.63 ml of acetone cooled at about −20° C., was added. The resulting reaction mixture was stirred for about 4 hours at −23° C. to −20° C. Crystals formed and were filtered, washed with 2 ml of ice-cold acetone and dried at 60° C./vacuum for about 1.5 hours. Prasugrel hydrogen sulfate form S1 (0.379 g) was obtained.

Example 50

Preparation of Crystalline Form S2 of Prasugrel Hydrogen Sulfate

To a solution of prasugrel base (0.204 g) in 2.5 ml of ethyl formate at 20-25° C., a dropwise solution of 29.3 µL conc. $H_2SO_4$ was added. An oily reaction mixture was obtained and seeded with small amount of prasugrel hydrogen sulfate form S1, but the seeding crystals dissolved. 0.1 ml of ethanol was added to obtain clear reaction mixture. Crystallization occurred within few minutes. Weak suspension was stirred at 20-25° C. for about 2 hours and cooled to 0-5° C. for about 2 hours. After 5 days at about −20° C., the suspension was stirred again at 8-10° C. for about 17 hours. The obtained crystals were filtered, washed with 2 ml of ethyl formate and dried at 40° C./vacuum for about 3 hours. Prasugrel hydrogen sulfate form S2 was obtained (0.127 g).

Example 51

Preparation of Crystalline Form S3 of Prasugrel Hydrogen Sulfate

To a suspension of prasugrel base (0.50 g) in 4 ml of ethyl acetate and 2 ml of 2-propanol, a solution of 75 µl 96% $H_2SO_4$ in 2 ml of ethyl acetate was added to obtain a mixture. The mixture was left in refrigerator at 2-8° C. After about 17 hours, crystals were formed. The suspension was stirred on ice bath for additional 6 hours and the obtained crystals were filtered and dried at 40° C./vacuum for 17 hours to yield Prasugrel hydrogen sulfate form S3 (0.19 g).

What is claimed is:

1. A crystalline Form I of Prasugrel hydrobromide according to formula I,

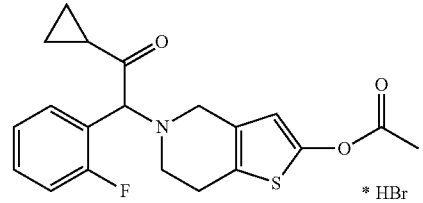

Formula I characterized by:
 an X-ray powder diffraction pattern having peaks at 7.8, 14.4, 16.9, 22.0 and 25.1 degrees two theta±0.2 degrees two theta;
 a solid-state $^{13}C$ NMR spectrum having peaks at 7.1, 11.2, 63.6, 123.7 and 203.4±0.2 ppm; or a combination thereof.

2. A crystalline Form IA of Prasugrel hydrobromide according to formula I,

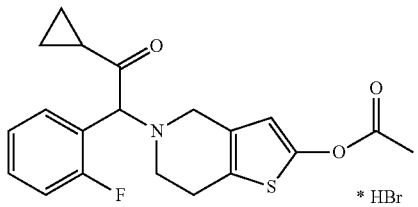

Formula I characterized by an X-ray powder diffraction pattern having peaks at 7.9, 8.1, 13.5, 14.6 and 25.2 degrees two theta±0.2 degrees two theta.

3. The crystalline Form I of Prasugrel hydrobromide according to claim 1, further characterized by an XRPD pattern substantially as depicted in FIG. 6 and/or by a solid-state 13C NMR spectrum substantially as depicted in FIG. 23.

4. The crystalline Form IA of Prasugrel hydrobromide according to claim 2, further characterized by an XRPD pattern substantially as depicted in FIG. 11.

5. A pharmaceutical composition comprising at least one crystalline form according to any of claims 1, 2 and 3-4, and at least one pharmaceutically acceptable excipient.

6. A method of producing a pharmaceutical composition comprising combining at least one crystalline form according to any of claims 1, 2 and 3-4, and at least one pharmaceutically acceptable excipient.

7. The crystalline Form I of Prasugrel hydrobromide according to claim 1, wherein the crystalline Form I is anhydrous.

8. The crystalline Form IA of Prasugrel hydrobromide according to claim 2, wherein the crystalline Form IA is anhydrous.

9. The crystalline Form I of Prasugrel hydrobromide according to claim 1 wherein the X-ray powder diffraction pattern has additional peaks at 13.5, 19.9, 23.6, 27.0 and 29.7 degrees two theta±0.2 degrees two theta.

10. The crystalline Form IA of Prasugrel hydrobromide according to claim 2 wherein the X-ray powder diffraction pattern has additional peaks at 16.8, 21.4, 23.7, 24.9 and 27.2 degrees two theta±0.2 degrees two theta.

* * * * *